United States Patent
Goldberg et al.

(10) Patent No.: US 6,296,606 B1
(45) Date of Patent: *Oct. 2, 2001

(54) PATIENT THERMAL SUPPORT DEVICE

(76) Inventors: Charles Goldberg, 11955 Eider Dr., Cincinnati, OH (US) 45246; David C. Newkirk, 16 Farmview, Harrison, OH (US) 45030; William Olson, 5360 Burgundy Pl., Fairfield, OH (US) 45014; Michael M. Donnelly, 3773 Middleton Ave., Cincinnati, OH (US) 45220; Robert G. Moll, 6221 N. Shadow Hill Way, Loveland, OH (US) 45140; Alan Gutwillig, 1703 Hulke Dr., Appleton, WI (US) 54915

(*) Notice: Subject to any disclaimer, the term of this patent is extended or adjusted under 35 U.S.C. 154(b) by 0 days.

This patent is subject to a terminal disclaimer.

(21) Appl. No.: 09/484,728

(22) Filed: Jan. 18, 2000

(51) Int. Cl.⁷ .................................................... A61G 11/00
(52) U.S. Cl. ............................................................ 600/22
(58) Field of Search ........................ 600/21–22; 128/736

(56) References Cited

U.S. PATENT DOCUMENTS

| | | |
|---|---|---|
| 3,158,150 | 11/1964 | Croasdaile . |
| 3,335,713 | 8/1967 | Grosholz et al. . |
| 3,387,600 | 6/1968 | Terzian . |
| 3,511,162 | 5/1970 | Truhan . |
| 3,618,734 | 11/1971 | Khan . |
| 3,776,217 | 12/1973 | van Galen et al. . |
| 3,782,362 | 1/1974 | Puzio . |
| 3,821,947 | 7/1974 | Schossow . |
| 3,858,570 | 1/1975 | Beld et al. . |
| 4,063,495 | 12/1977 | Duvlis . |
| 4,140,105 | 2/1979 | Duvlis . |
| 4,321,913 | 3/1982 | Maluta et al. . |
| 4,361,137 | 11/1982 | Grosholz . |
| 4,423,669 | 1/1984 | Bullock et al. . |
| 4,617,912 | 10/1986 | Beer et al. . |
| 4,750,474 | 6/1988 | Dukhan et al. . |
| 4,796,605 | 1/1989 | Sasaki et al. . |
| 4,809,677 | 3/1989 | Mackin et al. . |
| 4,846,783 | 7/1989 | Koch et al. . |
| 4,936,824 | 6/1990 | Koch et al. . |
| 5,162,038 | 11/1992 | Wilker . |
| 5,242,375 | 9/1993 | McDonough . |
| 5,308,310 | 5/1994 | Roff et al. . |
| 5,352,869 | 10/1994 | Barsky . |
| 5,453,077 | 9/1995 | Donnelly et al. . |
| 5,800,335 | 9/1998 | Koch et al. . |
| 5,817,003 | * 10/1998 | Moll et al. ............................ 600/22 |
| 5,876,323 | 3/1999 | Hodge et al. . |

FOREIGN PATENT DOCUMENTS

| | | |
|---|---|---|
| 2061704 | 7/1979 | (DE) . |
| 3607575 | 9/1987 | (DE) . |
| 0236851 | 2/1987 | (EP) . |
| 2031559 | 11/1970 | (FR) . |
| 1232048 | 5/1971 | (GB) . |
| 2175213 | 11/1986 | (GB) . |
| 122184 | 11/1974 | (JP) . |
| 90/09771 | 9/1990 | (WO) . |

OTHER PUBLICATIONS

Dec. 1971 Journal of Pediatrics "Air Curtain Incubator for use in a Intensive–Care Nursery", Musch, Adams and Sunshine, vol. 79, No. 6, pp. 1024–1030.

INFA–CARE 2000 brochure, Infa Care, Inc., 1972.

* cited by examiner

Primary Examiner—John P. Lacyk

(57) ABSTRACT

A patient warming apparatus includes a patient support and a canopy that moves upwardly and downwardly relative to the patient support. A radiant heater noves upwardly and downwardly with the canopy. The patient warming apparatus also includes a convective heater.

27 Claims, 19 Drawing Sheets

PATIENT THERMAL SUPPORT DEVICE

RELATED APPLICATION

This application is a continuation of application Ser. No. 09/088,350, filed on Jun. 1, 1998, now U.S. Pat. No. 6,036,634, which is a continuation of application Ser. No. 08/532,963, filed Sep. 25, 1995, now U.S. Pat. No. 5,759,149, which is a continuation-in-part of application Ser. No. 08/169,675, filed Dec. 17, 1993, now U.S. Pat. No. 5,453,077, the specification of which is herein incorporated by reference.

BACKGROUND AND SUMMARY OF THE INVENTION

The present invention relates to a support for patients and particularly to a patient thermal support device that provides an elevated and protected support surface for a patient and that protects and minimizes the disruption of the environment immediately surrounding the patient. More particularly, the present invention relates to a support device that controls the environment immediately surrounding the patient to minimize convective and evaporative heat loss from the patient so that the patient's own body warmth can keep the patient warm. The present invention can additionally be configured to warm a patient if desired using both convective and radiant warming techniques.

Incubators and radiant warmers have both been used to maintain the appropriate body temperature of small or premature infants. An incubator provides a generally transparent enclosure within which heated air is circulated to minimize the heat loss of the patient. In addition, heat is transferred to the patient via convective heat transfer. Incubators are typically provided with a large access door to allow for placement or removal of the infant in the incubator as well as supplemental access ways such as hand ports or small entry doors to permit routine care of the infant while minimizing heat loss from the incubator and the infant.

Radiant warmers provide for continuous and open access to an infant to accommodate a high frequency of intervention by the caregiver. Radiant warmers transfer heat to the patient via radiant heat transfer, typically from infrared heaters which emit infrared energy that is absorbed by the patient. The infrared heater is typically mounted to a support which is suspended above the patient support surface of the radiant warmer. Radiant warmers typically include no canopies or other enclosures that are commonly available on infant support devices to minimize the evaporative water losses of infants because such canopies or enclosures might obstruct the caregiver's access to the infant.

Patients can suffer from conditions that render it desirable to minimize contact between the patient's skin and objects, even including objects such as blankets. In addition, it is occasionally necessary for caregivers to have constant and ready access to the patient in certain critical care situations. What is needed is a patient support device that provides for continuous and open access to a patient while warming the patient should such warming be desired and that can be configured to minimize the evaporative water losses and resultant evaporative heat losses from the patient so that the patient can be uncovered while supported by the device.

According to the present invention, a patient support and environmental control apparatus is provided. The apparatus comprises a frame and an upwardly facing patient-support surface carried by the frame. In addition, an air curtain generator is mounted to the frame. The air curtain generator provides first and second curtains of air. The patient-support surface has a perimeter and the first and second curtains of air originate adjacent to the perimeter and converge at a point positioned to lie above the patient-support surface. The first and second curtains of air cooperate with the patient-support surface to define a patient space.

A patient can experience heat loss through any of the mechanisms of conductive, convective, and radiant heat transfer, as well as evaporative heat loss that results from the evaporation of moisture from the patient's body. Conductive heat loss accounts for a very low portion of the heat loss of a patient and radiant heat loss can be minimized by heating surfaces such as platforms and walls surrounding the patient. Evaporative and convective heat losses can be controlled by controlling the air near the patient. Factors that operate to influence the extent of evaporative and convective heat losses include the velocity of the air near the patient, the moisture content of the air near the patient, and the temperature of the air near the patient.

The air curtains cooperate with the patient-support surface to define a patient space that is protected from disturbances from outside of the patient space. The air curtains define an effective barrier to atmospheric influences outside of the patient space so that the patient space is generally unaffected by changes in the environment surrounding the patient thermal support device. At the same time, the patient thermal support device can be operated so that there are no physical barriers between the patient and the caregiver, providing the caregiver with continuous and open access to the patient even when the air curtains are in place.

In preferred embodiments, the patient thermal support device in accordance with the present invention uses air curtains to blanket the patient and to create a "thermoneutral" environment that insulates the patient from heat loss and allows the warmth generated by the patient to keep the patient warm. This device provides caregivers with unobstructed access to patients supported on the platform without the need to cover or in any other manner contact the patient.

A "dry" object can be warmed by blowing dry warmed air onto the object to effect a convective heat transfer. Likewise, a wet object can be warmed by blowing warmed air onto the object. The warming of the wet object can be maximized when the blowing air has a sufficient moisture content that there is no net loss of moisture by the object. However, a patient is more moist than any air that can be delivered to the patient by currently known techniques. As a result, as the velocity of the air engaging the patient increases, the evaporative moisture loss from the patient increases and the evaporative heat loss suffered by the patient increases.

In other words, when warmed air is delivered to the patient there are competing heating effects including a negative heating effect: due to evaporative heat losses and a positive heating effect due to the convective heat transfer. For example, when air at 38 degrees C that is not supplemented by moisture is delivered to the patient at a velocity below approximately 0.15 meters per second (0.49 feet per second), the heating due to convective heat transfer is greater than the heat loss due to evaporative moisture loss so that a net positive heat transfer to the patient occurs. However, when the air delivered to the patient is above approximately 0.15 meters per second (0.49 feet per second), the evaporative heat losses start to work against the convective gains so that at some higher threshold air velocity, the evaporative heat losses withdraw heat from the patient at a faster rate than convection supplies heat to the patient, so that increasing air velocity above the threshold velocity causes a net withdrawal of heat from the patient.

Although the primary purpose of the air curtains is to minimize the disturbance of the cloak of air surrounding the patient, the apparatus provides some convective heating by directing air from at least one additional air curtain toward the patient. The presently preferred embodiment of the patient thermal support device thus includes two opposing air curtains along the sides of the patient-support surface directed upwardly to form an air curtain "tent" above the patient resisting the ingress of air from outside of the patient space through the air curtains and into the patient space. Also, two additional air curtains originating at ends of the patient-support platform directed toward the patient are provided for convective heating of the patient.

In addition, for patients requiring less intervention, the patient thermal support device can be operated in an enclosed mode in which a canopy over the patient-support surface is lowered to engage side walls to enclose the patient space. Moisture can be added to the air curtains to minimize the moisture gradient between the patient and the cloak of air surrounding the patient. Although there is typically a large moisture gradient between the patient and the cloak, this gradient can be minimized by creating a moisture gradient between the air curtains and the cloak so that moisture is transferred from the air curtains to the cloak. Maximizing the moisture content of the cloak minimizes the moisture gradient between the patient and the cloak and minimizes the mass transfer from the patient to the cloak. Thus, evaporative moisture losses and the resultant evaporative heat losses are minimized by minimizing the moisture gradient between the patient and the cloak of air surrounding the patient. This is accomplished in the present invention by adding moisture to the air curtains.

In preferred embodiments, the apparatus also includes several additional features. For example, an exhaust opening at a point spaced-apart from the support surface is provided for withdrawing the air from the air curtains thus enhancing the integrity of the air curtains. The exhaust opening is preferably positioned near an "apex" of the envelope defined by the air curtains when the apparatus is operated in the enclosed mode.

The exhaust opening can be adjacent to the canopy that is positioned to lie above the patient. The canopy and exhaust opening can be vertically adjustable above the support surface so that the distance between the canopy and the support surface can be varied by the caregiver. The apparatus can also be provided with a position sensor for sensing the vertical distance between the exhaust opening and the surface. The air curtain generator can be configured so that the velocity of the air comprising the air curtains automatically varies with the distance between the support surface and the exhaust opening to further enhance the integrity of the air curtains.

The air curtain generator typically includes a channel or manifold containing heated air. The manifold can be positioned adjacent to an underside of a platform holding the patient support surface. The manifold can include an opening or bleeder hole that allows a portion of the heated air to escape and to be directed against a bottom surface of the platform. Heat transferred from the heated air to the bottom surface of the platform also heats the patient support surface through the platform and the mattress, thus providing an additional source of warmth for the patient.

Also in preferred embodiments, the apparatus includes an infrared radiant heater connected to the canopy to transfer heat to the patient via radiant heat transfer. The infrared radiant heater cooperates with the patient's own warmth, the warmed air that escapes the manifold to warm the patient support surface, and the warmed air of the air curtains delivered to the patient, to maintain the desired thermal environment for the patient. In some circumstances, the patient may not generate enough warmth to achieve the desired thermal environment. Also, it may not be desirable to warm the warmed air past a predetermined threshold temperature. The radiant heater can help to achieve and maintain the desired patient temperature when neither the patient nor the warmed air are sufficient for attaining and maintaining the desired patient temperature.

The apparatus in accordance with the present invention is provided with a main controller for controlling the temperature of the patient. The algorithm used by the main controller can control the temperature of the warmed air supplied to the air curtains and the power supplied to the infrared radiant heater. In preferred embodiments, the energy supplied by the radiant heater is minimized to minimize moisture loss due to the infrared energy supplied to the patient.

The algorithm is also designed so that the temperature of the warmed air comprising the air curtains does not exceed a predetermined maximum temperature. When the warmed air temperature approaches this predetermined maximum temperature, the radiant heater starts supplying energy to the patient. If more energy is required, the main controller will increase both the warmed air temperature and the energy provided by the radiant heater until the warmed air temperature reaches the predetermined maximum temperature. At this point, any further temperature increase is provided by the radiant heater. The main controller thus controls the air curtains and radiant heater to manipulate the patient space in order to control the convective and radiant heat transfer to the patient, ultimately to maintain the temperature of the patient at a desired temperature.

According to another aspect of the present invention, an apparatus is provided controlling operation of a patient warming device which includes a support surface for supporting a patient, a convective heater for supplying convective heat to warm the patient, a radiant heater for supplying radiant heat to warm the patient, and a humidifier for adding moisture to air adjacent the support surface. The apparatus includes a controller having a first output coupled to the convective heater and a second output coupled to the radiant heater for varying output power levels of the convective heater and the radiant heater, respectively, to maintain the patient located on the support surface at substantially a preselected temperature. The controller has a third output coupled to the humidifier to adjust an output from the humidifier. The apparatus also includes a temperature sensor having an output coupled to the controller to provide feedback to the controller so that the controller maintains the patient located on the support surface at substantially the preselected temperature. The apparatus further includes a humidity sensor having an output coupled to the controller. The controller adjusts the humidifier based on the output from the humidity sensor to permit the controller to maintain the humidity at substantially a preselected level.

In one illustrated embodiment, the temperature sensor is configured to be coupled to the patient. The apparatus includes an alarm coupled to the controller. The controller generating an alarm signal if the output from the temperature sensor changes above or below a predetermined level from the preselected or desired temperature. The apparatus further includes an input device coupled to the controller to permit a caregiver to adjust the preselected temperature and the preselected humidity level.

In addition to controlling the temperature of the patient, the apparatus in accordance with the present invention can also monitor the level of light to which the patient is exposed and can indicate to the caregiver when the patient is exposed to noise above a desired predetermined maximum noise level. The light monitor system and the noise monitoring system are controlled by the main controller.

Additional objects, features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description refers particularly to the accompanying drawing figures in which.

DETAILED DESCRIPTION OF THE DRAWINGS

Figure 1:
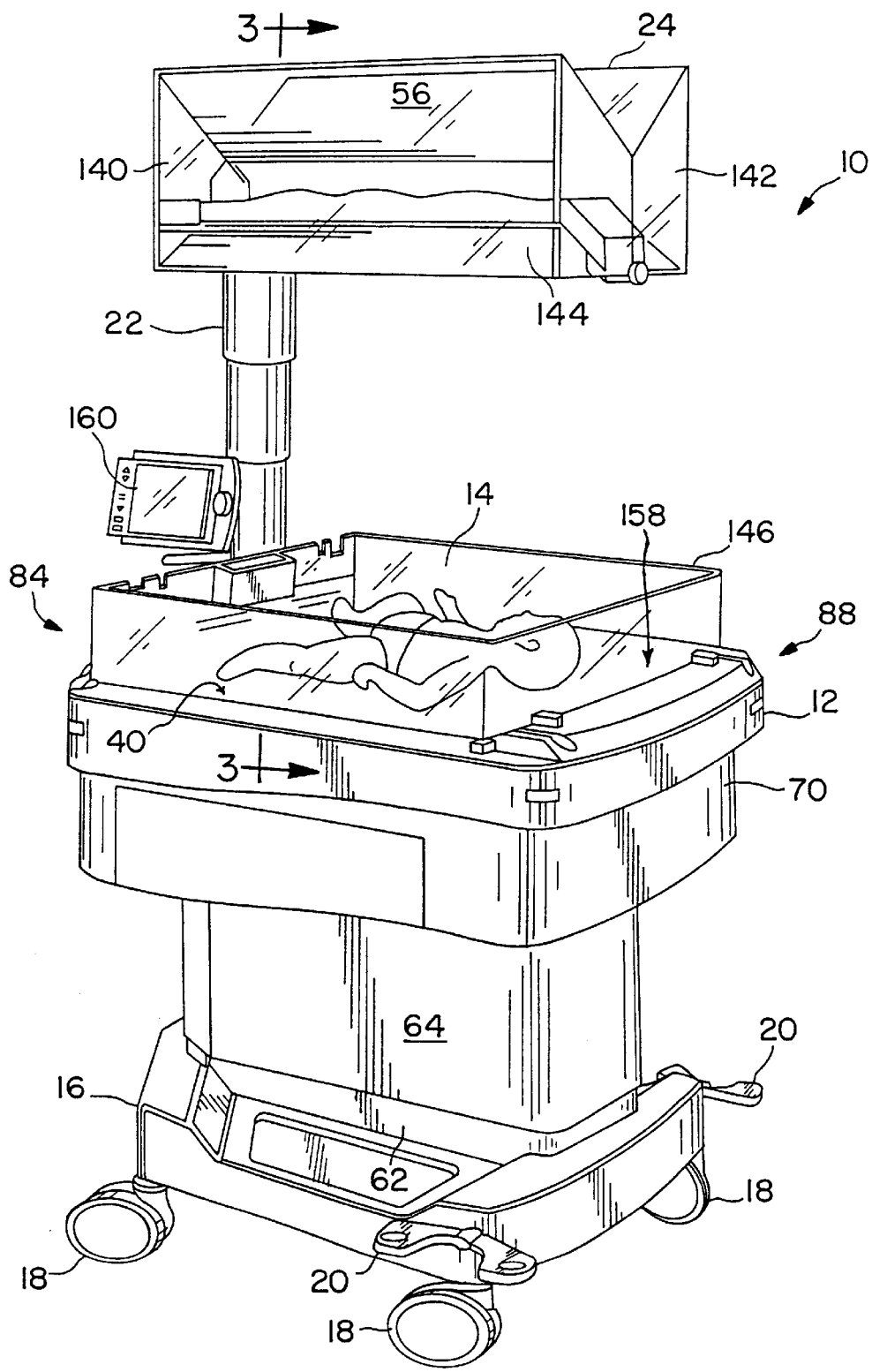
FIG. 1 is a perspective view of a patient thermal support device in accordance with the present invention showing a base supported on casters, a patient-support portion supported on the base and carrying a patient-support surface, a swivel display screen supported above the patient support surface by a canopy-support arm, and a canopy supported by the canopy-support arm above the patient-support surface.

A patient thermal support device 10 in accordance with the present invention is illustratively shown in FIG. 1. Device 10 includes a patient-support portion 12 for supporting a patient 14. For purposes of this specification, patient 14 is broadly defined to include anyone under the medical supervision of a physician.

A base portion 16 having castors 18, brake/steer pedals 20 coupled to castors 18, and a canopy-support arm 22 supporting a canopy 24 is mounted to patient-support portion 12. Canopy-support arm 22 can be mounted to a foot end 84 of patient-support portion 12, at a head end 88 of patient-support portion 12 as shown in FIG. 1, or to the sides of patient-support portion 12 as shown diagrammatically in FIGS. 5 and 6.

Base portion 16 can be provided with drawers (not shown) that slide through base portion 16 for use on both sides of device 10, the drawers having removable trays (not shown) with adjustable bins (not shown). Base portion 16 also includes telescoping members 62, 64 so that the height of base portion 16 and patient-support portion 12 is adjustable. Base portion 16 and patient-support portion 12 cooperate to define a frame.

Figure 2:
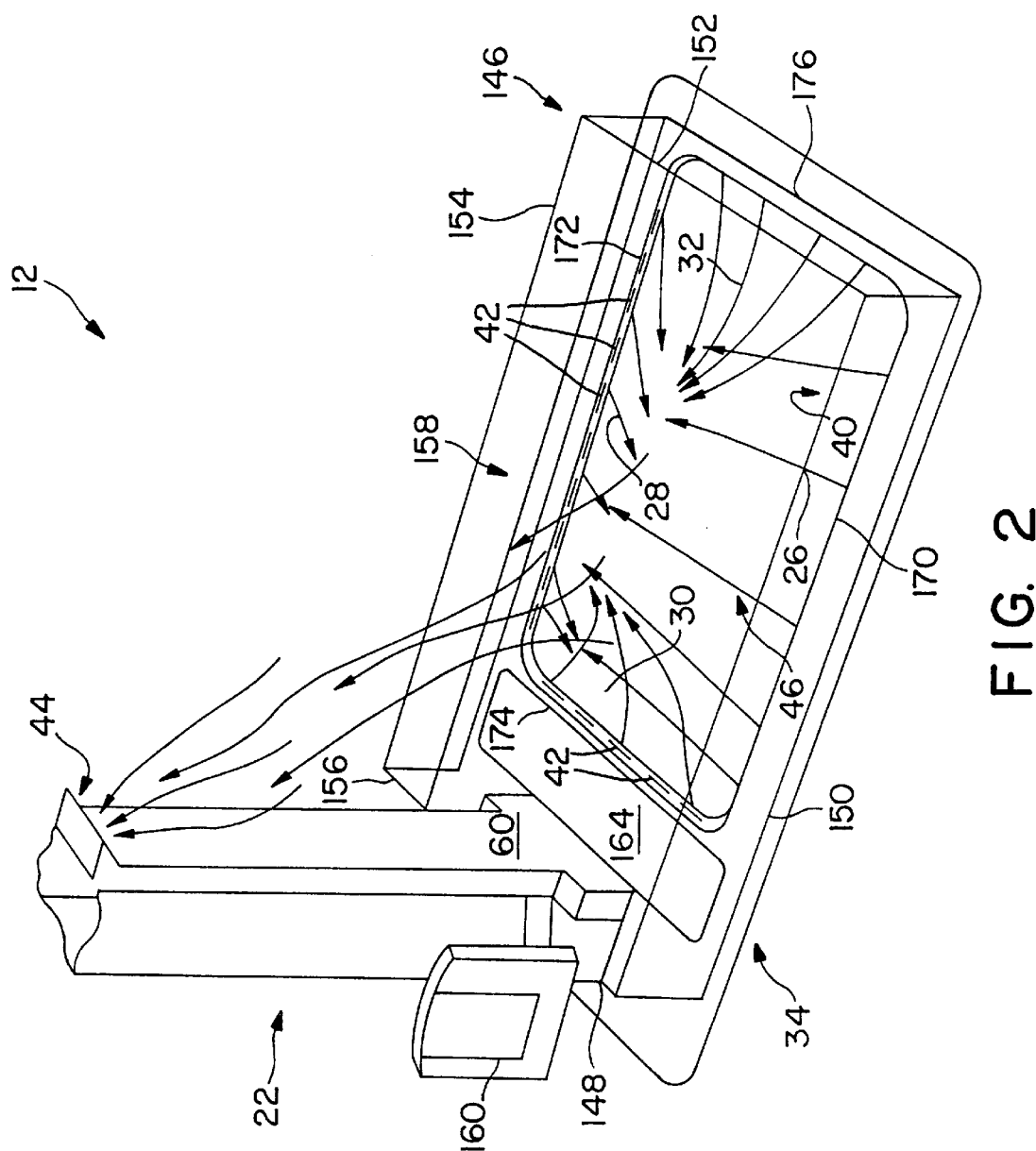
FIG. 2 is a perspective view of the patient-support surface and the canopy-support arm of FIG. 1 showing air curtains extending from the perimeter of the patient-support surface to an exhaust opening formed in a convective return of canopy-support arm, the exhaust opening being positioned to lie above the patient-support surface, and the air curtains cooperating with the patient-support surface to define a patient space.
Figure 3:
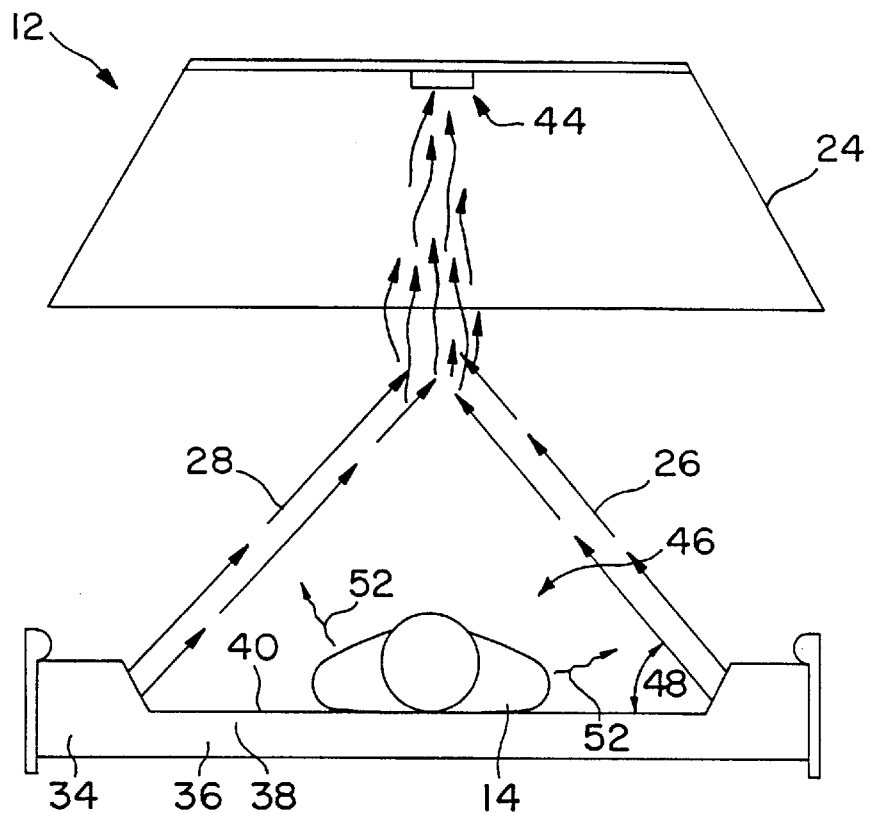
FIG. 3 is a diagrammatic dead sectional view taken along line 3—3 of FIG. 1 showing a canopy in a raised position, pivotable side walls pivoted to a down position, and a patient on the patient-support surface, the patient being positioned to lie in the patient space defined between the air curtains and the patient-support surface.

The preferred patient thermal support device 10 provides heated first and second air curtains 26, 28 directed upwardly from the sides of patient-support portion 12 as shown diagrammatically in FIGS. 2 and 3 to block the flow of air from outside of device 10 past air curtains 26, 28. In addition, device 10 can provide a heated third air curtain 30 along either the head or the foot of patient-support portion 12, preferably directed underneath air curtains 26, 28, and device 10 can be configured to provide a heated fourth air curtain 32 opposing third air curtain 30 as shown in FIG. 2.

Figure 14:
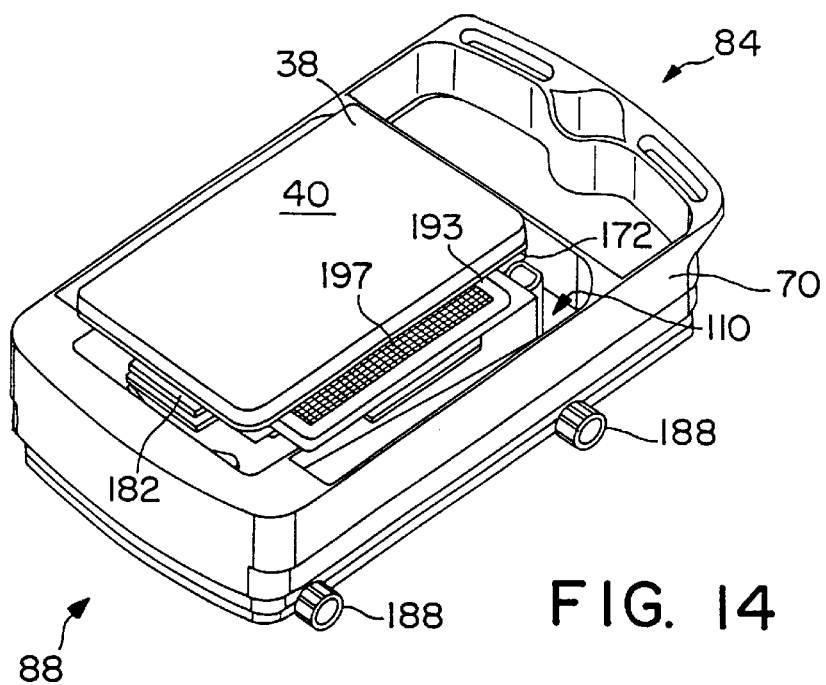
FIG. 14 is a perspective view of the tub showing a mattress carried by a mattress positioning assembly mounted in a mattress well of the tub.
Figure 15:
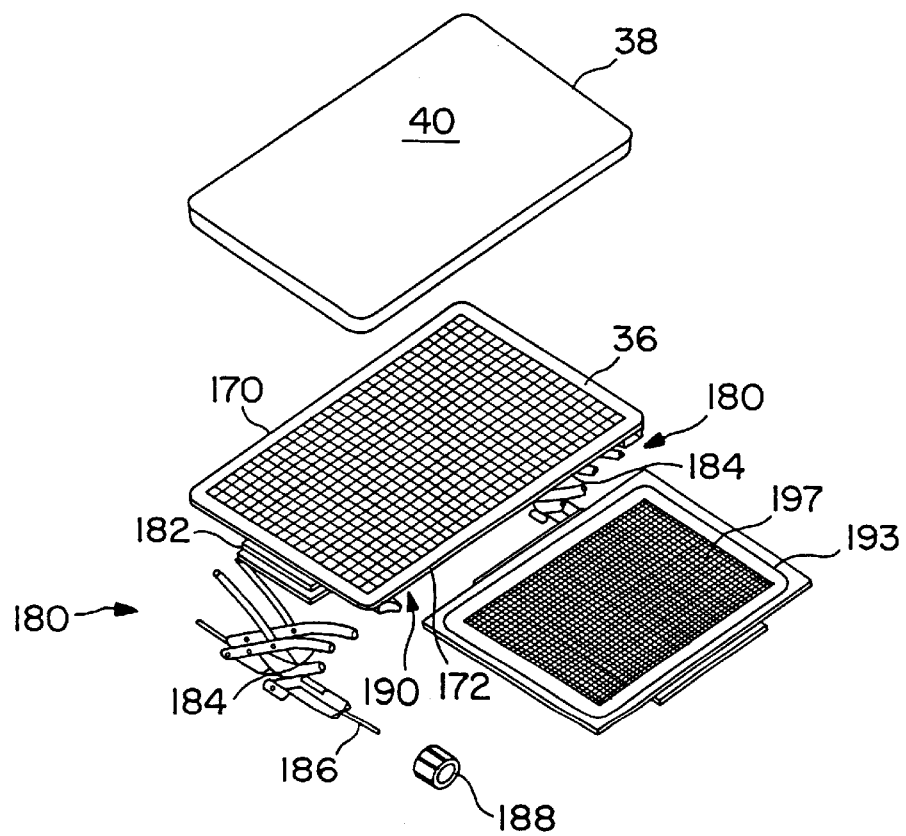
FIG. 15 is an exploded perspective view of the mattress and the mattress positioning assembly showing a platform carrying the mattress, load cells mounted to the platform, and extender assemblies mounted beneath the load cells.

Patient-support portion 12 of patient thermal support device 10 includes a deck 34 carrying a platform 36 shown diagrammatically in FIGS. 3–6 and shown in FIGS. 14 and 15. A mattress 38 having an upwardly-facing patient-support surface 40 rests on platform 36 and a plurality of air vents 42 surround the perimeter of mattress 38 as shown in FIGS. 2–6. Canopy-support arm 22 is formed to include an exhaust opening 44 that is vertically spaced-apart from patient-support surface 40. Air curtains 26, 28 extend generally from the perimeter of mattress 38 toward exhaust opening 44 to define a patient space 46 thereunder.

Figure 5:
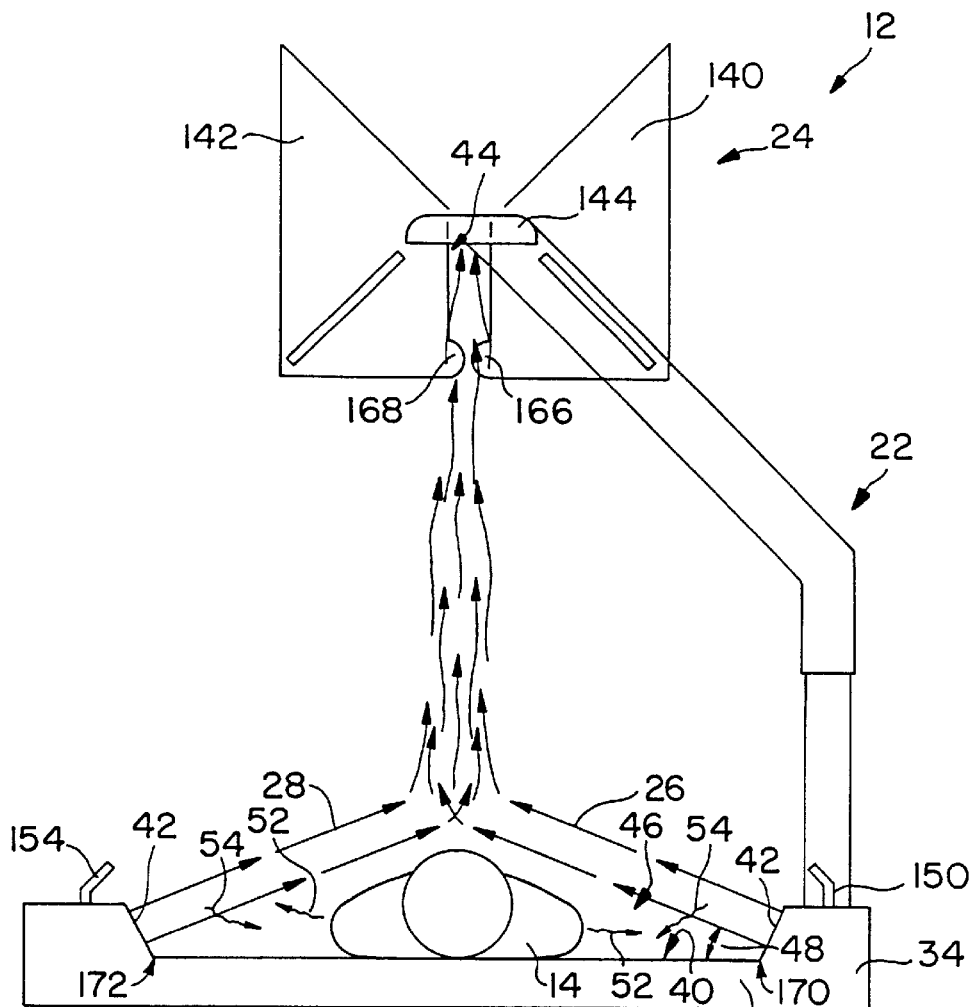
FIG. 5 is a view similar to FIG. 3 of a second embodiment of a patient thermal support device showing a canopy in a raised position, pivotable canopy side members pivoted upwardly, and slidable side walls moved to a down position to maximize the access of the caregiver to the patient.

Preferably, air curtains 26, 28 have an air velocity between 0.2 and 0.5 meters per second (0.66–1.6 feet per second) coming out of air vents 42 and a temperature of 42 degrees centigrade or less coming out of air vents 42. Also, air curtains 26, 28 are preferably directed at an angle 48 of 45 degrees above patient-support surface 40 as shown, for example, in FIG. 3 forming an air curtain "tent" above patient 14. An effective air curtain tent can be maintained when angle 48 is lowered as shown in FIG. 5 to any angle that does not result in direct impingement of air curtains 26, 28 on patient 14 and angle 48 can be raised as high as 90 degrees above patient-support surface 40 without eliminating the effectiveness of air curtains 26, 28 at blocking the flow of outside air into the tent.

Preferably, air curtains 26, 28 are not generally directed at patient 14. However, in preferred embodiments, air from air curtains 30, 32 is delivered to patient 14 in patient space 46 beneath air curtains 26, 28. Air curtains 30, 32 are configured so that the velocity of air delivered to patient 14 is no greater than approximately 0.15 meters per second (0.49 feet per second).

Although the preferred embodiment is configured as described above, air curtains 26, 28, 30, 32 can be configured so that any of the four air curtains 26, 28, 30, 32 is directed upwardly and any other of the four air curtains 26, 28, 30, 32 is directed into patient space 46. In addition, the angle formed between each air curtain 26, 28, 30, 32 and patient-support surface 40, such as angle 48 shown in FIG. 3, can differ for each air curtain 26, 28, 30, 32 so that all four air curtains 26, 28, 30, 32 are at different angles relative to patient-support surface 40.

Heat transfer to and from patient 14 can occur primarily through any of the mechanisms of conductive, convective, and radiant heat transfer, as well as through evaporative heat loss that accompanies the evaporation of moisture from patient 14. Conductive heat loss accounts for a very low portion of the heat loss from patient 14 and radiant heat loss can be minimized by heating surfaces such as platforms and walls surrounding patient 14. Evaporative and convective heat losses can be controlled by controlling the air in patient space 46. Factors that operate to influence the extent of evaporative and convective heat losses include the temperature and velocity of the air directed at patient 14 and the moisture content of the air in patient space 46 surrounding patient 14.

Directing heated air against an object that is initially at a temperature below that of the heated air can result in two competing heat transfer effects. The heated air can raise the temperature of the object through convection. At the same time, the heated air can cause moisture associated with the object to evaporate resulting in evaporative moisture losses and, as a result, evaporative heat losses. As the velocity of the air increases, the warming effect due to convection and the cooling effect due to evaporative heat losses both increase, but at different rates.

For example, air having no supplemental humidity at 38 degrees C directed against patient 14 will substantially warm patient 14 so long as the air is below a velocity of approximately 0.15 meters per second (0.49 feet per second) at patient 14. When the air delivered to patient 14 is above approximately 0.15 meters per second (0.49 feet per second), the evaporative heat losses start to work against the convective gains so that at some higher threshold air velocity, the evaporative heat losses withdraw heat from patient 14 at a faster rate than convection supplies heat to patient 14, so that increasing air velocity above the threshold velocity causes a net withdrawal of heat from patient 14.

Air curtains 26, 28 reduce the movement of air from outside of patient space 46 through air curtains 26, 28 and into patient space 46. Air curtains 26, 28 minimize the ingress of air currents from outside of patient space, thereby controlling patient space 46. Air curtains 26, 28 thus isolate patient 14 from the air outside of patient space 46 defining a "thermo-neutral" environment and acting as a blanket allowing the warmth generated by patient 14 to maintain the temperature of patient 14 at a desired temperature.

Patient 14 typically has a far higher moisture content than is found in the air of patient space 46 surrounding patient 14. This moisture gradient can result in significant evaporative moisture losses and evaporative heat losses from patient 14, designated by arrows 52 in FIGS. 3–6, even when no moving air is directed at patient 14. Air curtains 26, 28 minimize evaporative moisture losses by containing the moisture lost by patient 14 in patient space 46 to minimize the moisture gradient between patient 14 and patient space 46.

Figure 4:
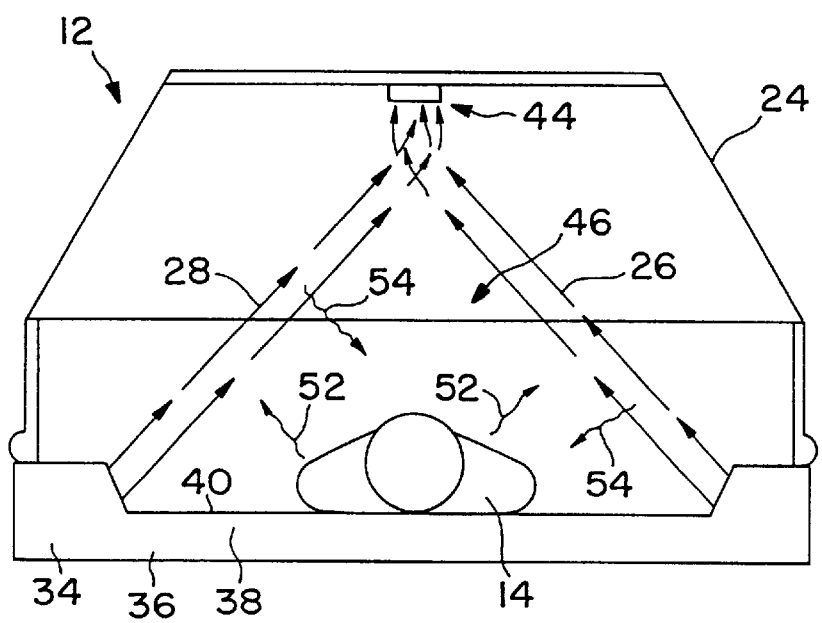
FIG. 4 is a view similar to FIG. 3 showing the patient thermal support device in an enclosed position having the canopy in a down position over the patient-support surface and the pivotable walls in the up position to enclose the patient in the patient thermal support device.
Figure 6:
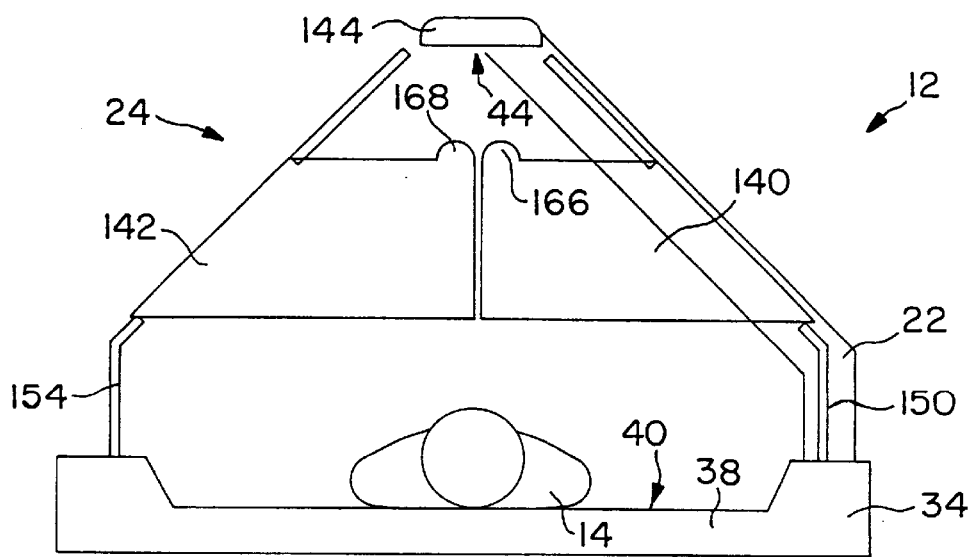
FIG. 6 is a view similar to FIG. 5 showing the patient thermal support device in an enclosed position having the canopy in a down position over the patient-support surface, the canopy side members pivoted downwardly, and the slidable side walls moved to an up position to enclose the patient.

In addition, patient thermal support device 10 can be operated in an enclosed mode as shown diagrammatically in FIGS. 4 and 6 having air curtains 26, 28, 30, 32 humidified to increase the moisture content of air curtains 26, 28, 30, 32. Increasing the moisture content of air curtains 26, 28, 30, 32 creates a second moisture gradient between air curtains 26, 28, 30, 32 and patient space 46. This second moisture gradient causes moisture from air curtains 26, 28, 30, 32 designated by arrows 54 in FIGS. 4 and 6 to transfer to patient space 46. Transferring moisture into patient space 46 further reduces the moisture gradient between patient space 46 and patient 14, and as a result, further reduces evaporative moisture losses and evaporative heat losses from patient 14.

Air curtains 30, 32 can be configured to direct air against patient 14, as shown in FIG. 2, preferably at a velocity of approximately 0.15 meters per second (0.49 feet per second) or less at patient 14 so that this air warms patient 14. As described hereinafter, the air in air curtains 26, 28, 30, 32 can be heated so that convective heat transfer from air curtains 30, 32 can augment the warmth generated by patient 14 to warm patient 14 isolated in patient space 46.

Patient thermal support device 10 can additionally be provided with a radiant warmer 56 as shown in FIG. 1. Radiant warmer 56 generates and directs infrared radiation at patient 14 to warm patient 14. In preferred embodiments, heated air in air curtains 26, 28, 30, 32 is not at a temperature higher than 42 degrees C when coming out of air vents 42. When the warmth generated by patient 14 and the heated air are insufficient to attain the desired temperature of patient 14, radiant warmer 56 can be used to provide additional warmth to patient 14. As can be seen, radiant warmer 56 is a secondary supplement that augments both the warmth generated by patient 14 and the convective heating provided by heated air from air curtains 30, 32 to warm patient 14 to a desired temperature.

Deck 34 of patient thermal support device 10 can be configured as shown in FIG. 2 having a convective return 60 extending upwardly from deck 34 to exhaust opening 44, a side wall 146 cooperating with convective return 60 to define an inner deck 158, and a warmed storage area 164 on inner deck 158 adjacent to patient-support surface 40 for the storage of items (not shown) that may be used on patient 14. For example, alcohol wipes, probes, and saline bottles could all be stored in the warmed storage area. Because warmed storage area is under canopy 24, items stored will remain relatively warm and at a temperature close to the temperature of the air surrounding patient 14. Keeping such items at or near the temperature of the air surrounding patient 14 reduces the "cold shock" experienced by patient 14 upon initial contact of the items with the skin of patient 14.

Patient-support portion 12 can also be provided with a rotating display 160 as shown in FIGS. 1 and 2. Display 160 is located generally at the waist level of an adult caregiver although the vertical position of display 160 is adjustable with changes in height of base portion 16. In preferred embodiments, rotating display 160 is pivotably mounted to canopy-support arm 22 to pivot from side to side of device 10, and is positioned to lie outside of inner deck 158.

Patient-support portion 12 includes a tub 70 having a mattress well 72 surrounded by an air curtain generator or air handling assembly 74 as shown in FIGS. 7–11 and 13. Deck 34 is carried on tub 70 and canopy-support arm 22 is supported by both deck 34 and tub 70. Air handling assembly 74 includes a heater 76, a fan 78, a fan motor 79, a filter 80, a divider 82, and various channels or pathways formed in tub 70 as shown in FIGS. 7–11.

Figure 7:
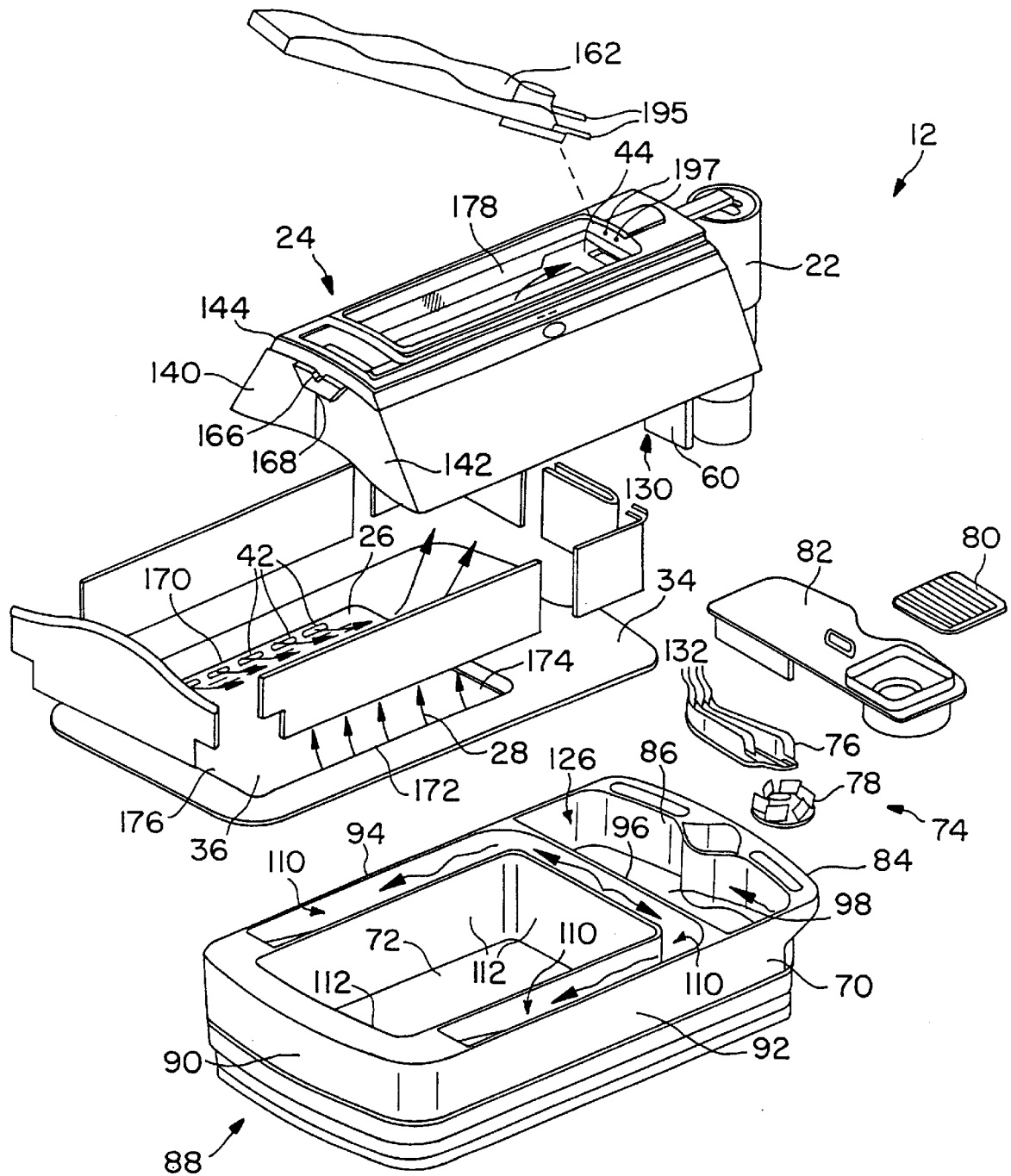
FIG. 7 is an exploded perspective view of the patient-support portion of the patient thermal support device of FIG. 1 showing a tub formed to include a tank-like mattress well and an air handling assembly formed around the mattress well, a deck over the tub having a plurality of vents around a platform formed on the deck, removable walls surrounding the deck, and a canopy movably coupled to the canopy-support arm connected to the tub.

Tub 70 includes a foot end 84 having a wall 86, a head end 88 having a wall 90, and two elongated sides 92, 94 therebetween as shown in FIG. 7. A transverse bulkhead 96 extends between the sides 92, 94 and is spaced-apart from walls 86, 90 to define a space containing an air make-up compartment 98 and an air mixing space 126 between bulkhead 96 and wall 86.

Figure 8:
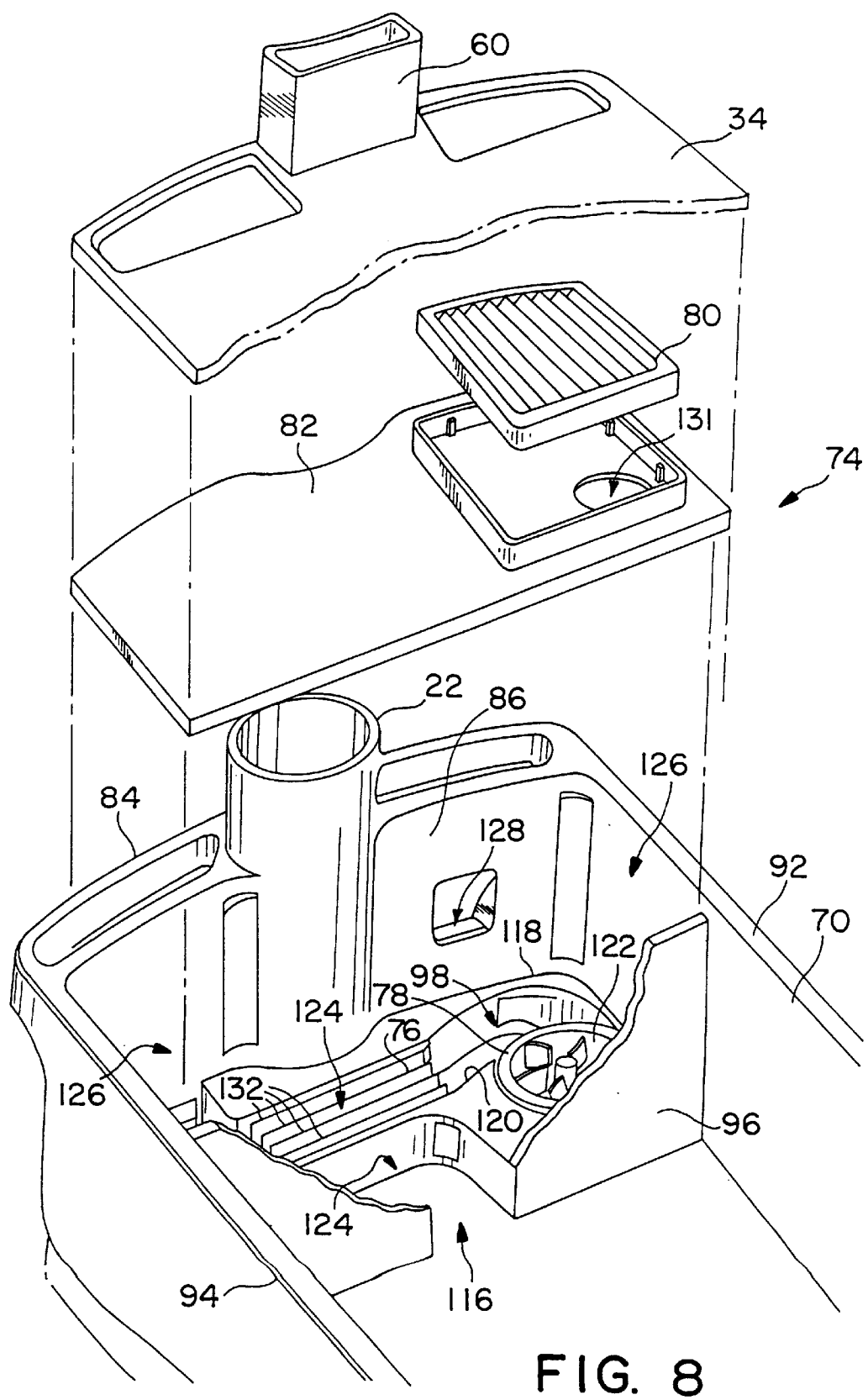
FIG. 8 is an enlarged exploded perspective view of a foot end of the tub showing elements of the air handling assembly.
Figure 9:
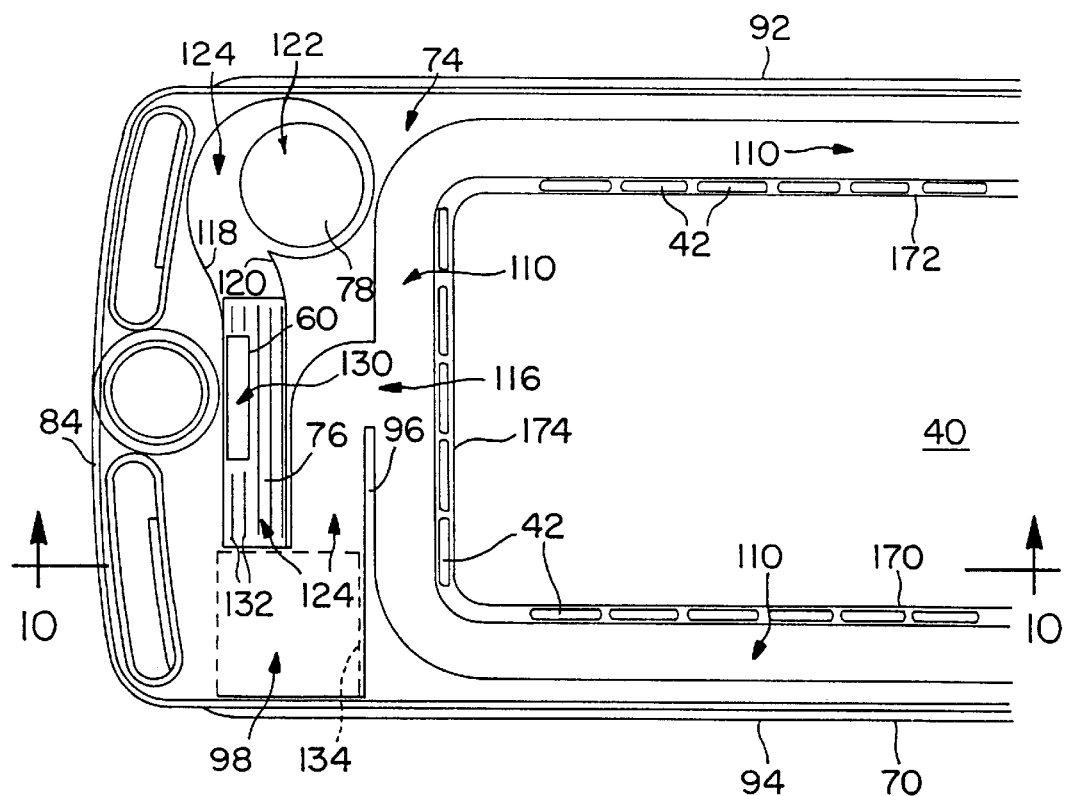
FIG. 9 is a top plan view with portions broken away of the foot end of the tub showing elements of the air handling assembly.

Tub 70 further includes an inner wall 112 defining mattress well 72 as shown in FIG. 7. Inner wall 112 cooperates with bulkhead 96 and sides 92, 94 to define a manifold or air delivery channel 110 in fluid communication with an opening 116 formed in bulkhead 96 as shown in FIGS. 8 and 9. Deck 34 is formed to include openings or vents 42 in fluid communication with air delivery channel 110. Air delivery channel 110 receives air from air make-up compartment 98 through opening 116 in bulkhead 96 and delivers the air to vents 42. Vents 42 direct the air from channel 96 to form air curtains 26, 28, 30, 32.

Although air delivery channel 110 is shown extending adjacent to bulkhead 96 and sides 92, 94, tub 70 can be formed so that air delivery channel 96 additionally extends adjacent to wall 90 on head end 88 between wall 90 and inner wall 112 so that channel 96 surrounds mattress well 72 to deliver air from air make-up compartment 98 to air curtains 26, 28, 30, 32. In addition, air delivery channel 10 and vents 42 can be configured so that not all air curtains 26, 28, 30, 32 are available. For example, channel 110 and vents 42 can cooperate so that only air curtains 26, 28 along sides 170, 172 of platform 36 are present by forming vents 42 only along sides 170, 172 of platform 36. Another potential configuration could have air delivery channel 110 and vents 42 configured so that only air curtains 30, 32 along ends 174, 176 of platform 36 are present, for example, by forming vents 42 only along ends 174, 176 of platform 36. However, it is presently preferred that four air curtains are present, including air curtains 26, 28 along sides 170, 172 of platform 36 directing air above patient 14 and air curtains 30, 32 along the ends 174, 176 of platform 36 delivering warm air to patient 14.

In preferred embodiments, the top of inner wall 112 of patient-support portion 12 can be spaced-apart from the bottom of platform 36 to form a bleeder hole (not shown) therebetween. The bleeder hole can be configured to allow a small amount of heated air from air delivery channel 110 to bleed into mattress well 72. This heated air can heat the bottom surface of platform 36 consequently heating patient-support surface 40 by conduction through platform 36 and mattress 38. Although the top of wall 112 can be spaced apart from platform 36 to form bleeder hole, bleeder hole can also be an opening formed in wall 112. Bleeder hole can be any opening, channel, or conduit through which heated air enters mattress well 72 beneath platform 36.

Air make-up compartment 98 holds the heater 76, fan 78, filter 80, and divider 82 as shown best in FIGS. 7–10. Air make-up compartment 98 includes first and second walls 118, 120 defining a fan compartment 122 and cooperating with bulkhead 96 to define an air make-up channel 124. First and second walls 118, 120 are shorter than wall 86, sides 92, 94, and bulkhead 96. Divider 82 rests on top of walls 118, 120. The bottom of divider 82 defines a top of air make-up channel 124 and the top of divider 82 cooperates with wall 86, sides 92, 94, and bulkhead 96 to define an air-mixing space 126.

Wall 86 along foot end 84 of tub 70 is formed to include a fresh air inlet 128 in fluid communication with air-mixing space 126 as shown in FIG. 8. In addition, exhaust opening 44 formed in canopy-support arm 22 and positioned to lie above patient-support surface 40 to receive air from air curtains 26, 28, 30, 32 is in fluid communication with a convective return opening 130 through convective return 60 and is in fluid communication with air-mixing space 126 as shown in FIGS. 7–10. Consequently, air from air curtains 26, 28, 30, 32 travels through exhaust opening 44, through convective return 60, and through convective return opening 130 to mix with fresh air from fresh air inlet 128 in air-mixing space 126 above divider 82.

Figure 10:
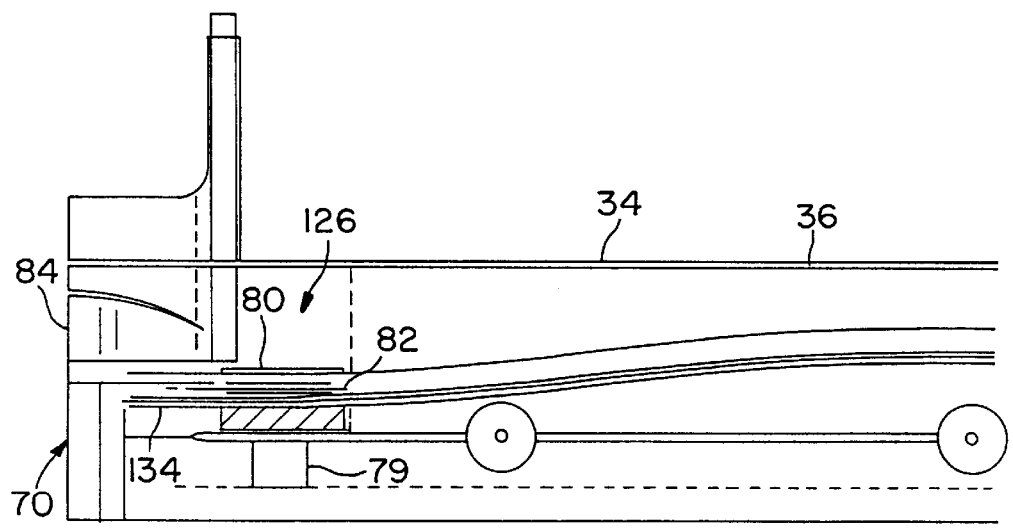
FIG. 10 is a sectional view taken along line 10—10 of FIG. 9 showing elements of the air handling assembly.

Fan 78 is rotatably received in fan compartment 122 and fan motor 79 is positioned to lie in tub 70 beneath fan 78 as shown in FIG. 10. Upon rotation of fan 78, the mixture of fresh air and recirculated air is drawn from air-mixing space 126, through filter 80 and a filter opening 131 formed in divider 82, to fan compartment 122. Fan 78 pressurizes the air in fan compartment 122 and forces the pressurized air into air make-up channel 124. Bulkhead 96 is formed to include an opening 116 in fluid communication with air make-up channel 124 and air delivery channel 110. The pressurized air in air make-up channel 124 travels through opening 116 in bulkhead 96 into air delivery channel 110, and then through vents 42 to form air curtains 26, 28, 30, 32.

Fan 78 additionally pulls return air from air curtains 26, 28, 30, 32 along with air from outside of patient space 46 into exhaust opening 44 as shown in FIG. 2. The return air then travels through convective return 60 and convective return opening 130 to air-mixing space 126 as shown in FIGS. 8–10. In addition to drawing return air into air-mixing space 126, fan 78 draws fresh air into air-mixing space 126 through fresh air inlet 128 as shown in FIG. 8. Fresh air inlet 128 can be provided with a damper (not shown) to adjust the effective size of fresh air inlet 128 and thus adjust the ratio of fresh air to return air that is drawn into air-mixing space 126 and subsequently circulated into air curtains 26, 28, 30, 32. Satisfactory results have been achieved when the air in air-mixing space 126 includes approximately 80% return air from convective return 60 and 20% fresh air from fresh air inlet 128.

In preferred embodiments, patient support portion 12 includes sensors (not shown) for detecting when one or more of vents 42 are blocked. For example, the velocity of air at a vent 42 could be detected by two spaced-apart elements (not shown) that are typically biased at different power levels so that the elements are at different temperatures. The power to the elements can be removed while air flows across the elements and the temperature difference between the elements can be measured. Variations of the temperature difference between the two elements could signify that air flow by one element is disrupted by, for example, a toy or blanket blocking vent 42. The patient thermal support device 10 can be configured to alert the caregiver to this potential problem.

Air make-up compartment 98 additionally includes heater 76 positioned to lie between first and second walls 118, 120 in air make-up channel 124 as shown in FIGS. 7–10. As air from fan 78 passes between fins 132 of heater 76, the air is warmed. The temperature of the air after passing over heater 76 can be varied by varying the temperature of heater fins 132.

Figure 11:
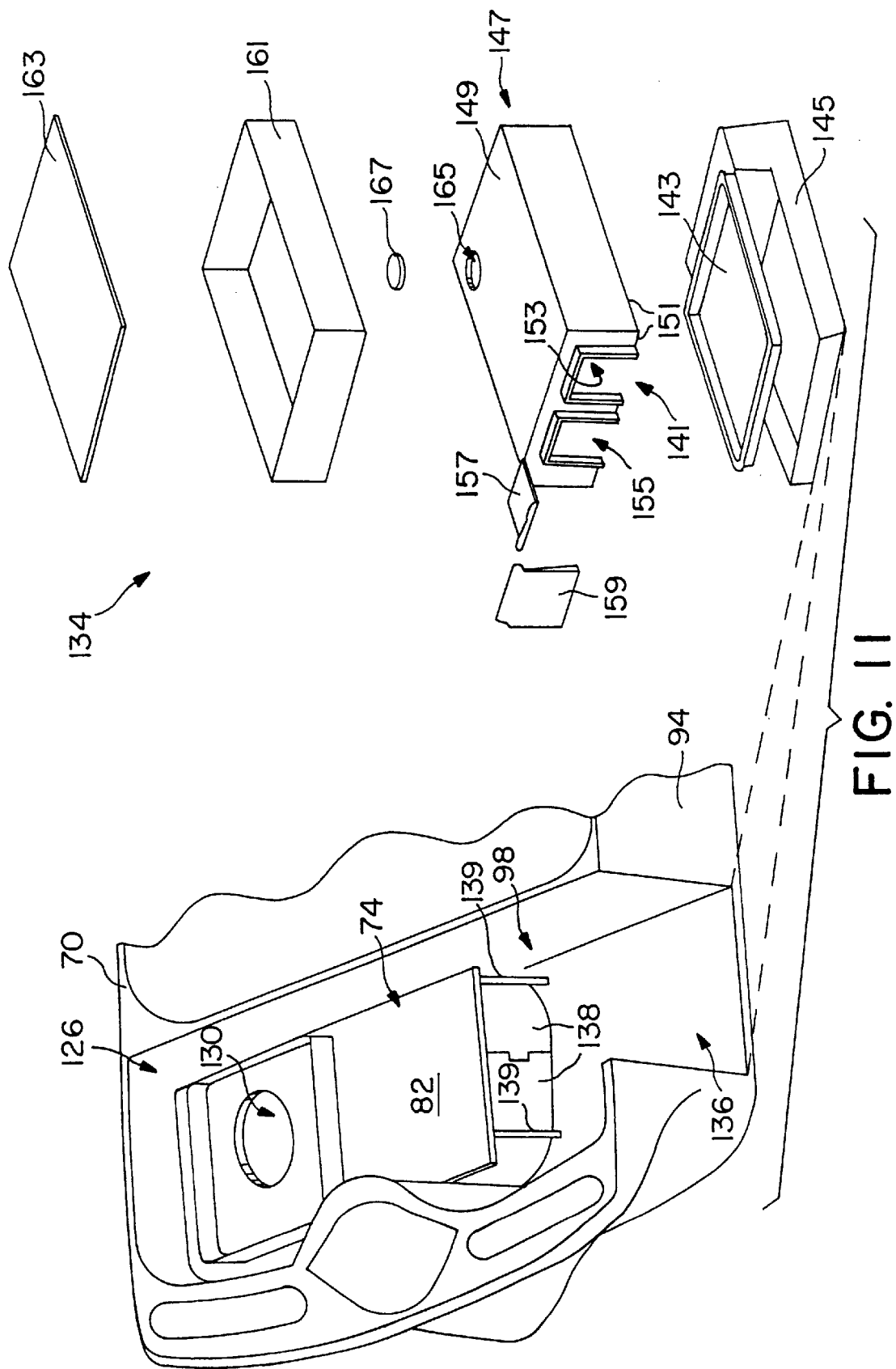
FIG. 11 is an enlarged exploded perspective view of the foot end of the tub showing the air handling unit and the elements of the humidifier.

Air make-up compartment 98 can also be provided with a humidifier 134 for adding moisture to the air in air make-up channel 124 as shown in FIGS. 9–11. Humidifier 134 is positioned to lie in air make-up channel 124 along the air flow path past heater 76 as shown in FIGS. 9 and 10. In preferred embodiments, humidifier 134 is a module that can be easily installed and removed from air make-up compartment 98 through opening 136 formed in tub 70 as shown in FIG. 11. Air handling assembly 74 can be provided with swinging doors 138 that are spring loaded and yieldably biased to a closed position as shown in FIG. 11. When doors 138 are in the closed position, doors 138 define an end of air make-up channel 124. When humidifier 134 is installed in air make-up compartment 98, camming engagement of humidifier 134 and doors 138 causes doors 138 to move to open positions so that a chamber 141 of humidifier is in fluid communication with air make-up channel 124 and defines a portion thereof.

Illustrative humidifier 134 includes an evaporator tray 143 having a heater (not shown), the heater and tray 143 being carried by a base 145 as shown in FIG. 11. Tray 143 cooperates with cabinet 147 having a top 149 and a wall 151 about the perimeter of top 149 to define chamber 141. Wall 151 is formed to include an entrance 153 and an exit 155. A door 157 is pivotably coupled to wall 151 adjacent entrance 153 to cover entrance 153 and a door 159 is coupled to wall 151 adjacent exit 155 to cover exit 155. When humidifier 134 is installed in air make-up compartment 98, camming engagement of tabs 139 on air handling assembly 74 and doors 157, 159 causes doors 157, 159 to move to open positions so that chamber 141 of humidifier 134 is in fluid communication with air make-up channel 124 and defines a portion thereof.

Humidifier 134 also includes a reservoir 161 and a reservoir lid 163 illustratively positioned above cabinet 147 for containing a water supply for humidifier 134 as shown in FIG. 11. Top 149 of cabinet 147 is formed to include an opening 165 and reservoir 161 includes a companion opening (not shown) in fluid communication with opening 165 through a flow regulator 167. Although illustrative reservoir 161 is a tank positioned above cabinet 147 inside of air make-up compartment 98, reservoir 161 can be any source of water in fluid communication with tray 143 and can be positioned to lie inside or outside of tub 70. For example, reservoir 161 could be a bag (not shown) filled with water and hanging from side 94 of tub 70.

Evaporator tray 143 is heated to vaporize water on tray 143 and to form water vapor over tray 143. The pressurized air in air make-up channel 124 passes through entrance 153 and into chamber 141. The pressurized air then carries the water vapor from over tray 143, through exit 155, into air-make-up channel 124, through opening 116 in bulkhead 96, to air delivery channel 110 and into air curtains 26, 28, 30, 32. Thus, by installing humidifier 134 into air make-up compartment 98, air delivery channel 110 is effectively expanded to include chamber 141 and the air in air curtains 26, 28, 30, 32 is humidified to increase the moisture content of air curtains 26, 28, 30, 32.

As described above, patient thermal support device 10 can be operated in an enclosed mode minimizing the air from outside of patient space 46 drawn into exhaust opening 44 and maximizing the amount of recirculated air in air curtains 26, 28, 30, 32. As the proportion of recirculated air pulled by fan 78 into air make-up compartment 98 from air-mixing space 126 increases, the moisture content of the air in air curtains 26, 28, 30, 32 increases.

In preferred embodiments, canopy-support arm 22 includes telescoping members so that canopy 24 is vertically movable relative to patient-support surface 40 between the raised position shown in FIGS. 1, 3, and 5 and the enclosed position shown in FIGS. 4 and 6. Exhaust opening 44 is movable with canopy 22. Canopy-support arm 22 encloses a sensor 234 that detects the vertical position of canopy 24 relative to patient-support surface 40.

As described above, air curtains 26, 28, 30, 32 originate at air vents 42 along the perimeter of patient-support surface 40 and the air from air curtains 26, 28, 30, 32 is drawn away through exhaust opening 44. As exhaust opening 44 moves relative to patient-support surface 40 and air vents 42, the rotational speed of fan 78 can be varied, thereby varying the velocity of air comprising the air curtains as well as varying the suction at exhaust opening 44 which pulls the air comprising air curtains 26, 28, 30, 32 through exhaust opening 44. For example, as exhaust opening 44 is moved farther from vents 42, rotational speed of fan 78 can be increased to increase the velocity of the air comprising air curtains 26, 28, 30, 32 and to increase the suction at exhaust opening 44. This increased rotational speed of fan 78 thus assures the integrity of air curtains 26, 28, 30, 32 even when exhaust opening 44 is moved away from patient-support surface 40.

Patient thermal support device 10 in accordance with the present invention can also be provided with side wall 146 including side wall portions 148, 150, 152, 154, 156 as shown in FIGS. 1–6 to provide additional protection for patient 14. Side wall portions 148, 150, 152, 154, 156 are pivotable between an upward enclosed position as shown diagrammatically in FIG. 4 for side walls 150, 154, and a down-out-of-the-way position shown diagrammatically in FIG. 3 maximizing the access of the caregiver to patient 14.

Alternatively, side wall portions 148, 150, 152, 154, 156 can be slidably mounted to tub 70 to slide between an upward enclosed position as shown diagrammatically in FIG. 6 for side walls 150, 154, and a down-out-of-the-way position shown diagrammatically in FIG. 5 maximizing the access of the caregiver to patient 14. In addition, canopy 24 can include two elongated spaced-apart canopy side members 140, 142 and an elongated support 144 sandwiched therebetween as shown in FIGS. 1, 5, and 6. Support 144 is connected to the canopy-support arm 22 and each canopy side member 140, 142 is pivotably connected to support 144 for pivoting movement relative to support 144 between a down position generally parallel to the patient-support surface shown in FIG. 6 and an up position maximizing access to the patient space 46 as shown in FIG. 5.

Thus, patient thermal support device 10 can be moved between the enclosed position of FIGS. 4 and 6 having side wall portions 148, 150, 152, 154, 156 moved to the up position and canopy 24 in the lowered position to filly enclose patient 14 and the position of FIGS. 3 and 5 having side wall portions 148, 150, 152, 154, 156 in the down-out-of-the-way position and canopy 24 in the raised position to maximize the caregiver's access to patient 14. In addition, canopy side members 140, 142 can be pivoted upwardly to provide the caregiver with even greater access to patient 14 as shown in FIG. 5.

When the patient thermal support device 10 is operated in the enclosed mode as shown in FIGS. 4 and 6, the return air is comprised almost entirely of air from the air curtains. As can be seen, as this air circulates through the device 10, the same air will make several passes over humidifier 134. As a result, the moisture added to the recirculating air in air curtains 26, 28, 30, 32 can be increased, maximizing the moisture gradient between the air in air curtains 26, 28, 30, 32 and patient space 46. The maximized moisture gradient between air curtains 26, 28, 30, 32 and patient space 46 will maximize the moisture transfer from air curtains 26, 28, 30, 32 to patient space 46 and minimize the moisture gradient between patient 14 and patient space 46, thus minimizing the evaporative heat losses of patient 14.

When patient thermal support device 10 fully encloses patient 14 as shown in FIGS. 4 and 6, it may be advantageous to reduce the velocity of the air in air curtains 26, 28, 30, 32. Although the rotational speed of fan 78 could be reduced to reduce the velocity of the air, it has been found that the increased air pressure within patient thermal support device 10 caused by closure of device 10 when in the fully enclosed position results in an increase of the pressure drop across fan 78. This increased pressure drop results in a satisfactory reduction of the velocity of air in the system without any adjustment of the rotational speed of fan 78.

Figure 12:
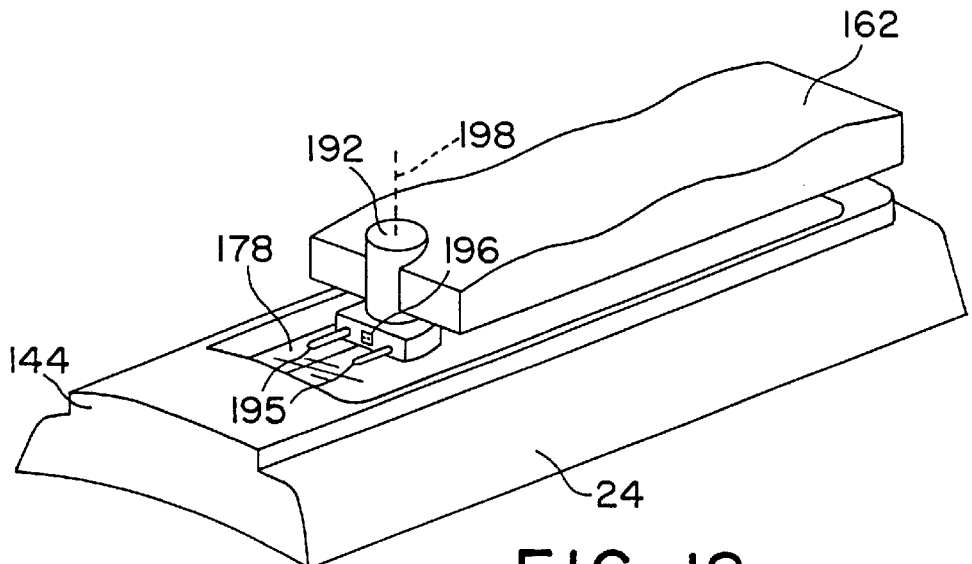
FIG. 12 is an exploded perspective view of the canopy and a portable accessory unit docking with the canopy, the assessory unit including a pivotable coupling having rearwardly projecting mounting pins and a plug for electrically connecting to a socket in the canopy.
Figure 13:
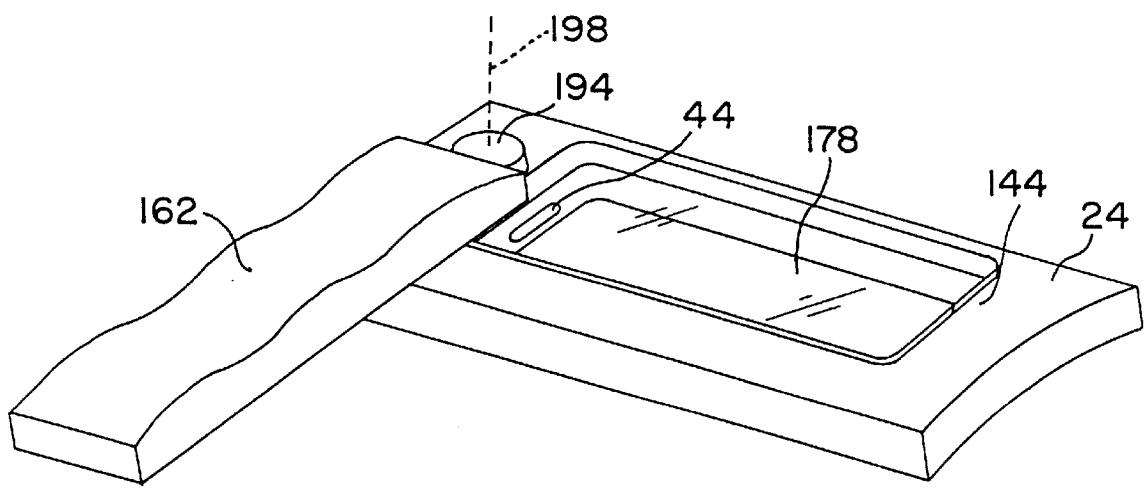
FIG. 13 is a view similar to FIG. 12 of a second embodiment of a canopy and a portable accessory unit, the canopy including a pivota.ble coupling and the accessory unit including pins (not shown) and a plug (not shown) connected to the pivotable coupling, the accessory being pivoted away from the canopy to an out-of-the-way position exposing a radiolucent x-ray window.

Canopy 24 can also be provided with a radiolucent x-ray window 178 positioned to lie above patient-support surface 40, as shown in FIGS. 7, 12, and 13, for use during fluoroscopic procedures. X-ray window 178 is configured to carry an x-ray generator (not shown). Mattress 38 can be raised above vents 42 by a mattress positioning assembly 180 to receive an x-ray cassette holder or tray 193 as shown in FIGS. 14 and 15. Mattress 38 is typically lowered back beneath vents 42 during use after tray 193 is received by mattress positioning assembly 180. Use of x-ray window 178 allows for the completion of fluoroscopic procedures on patient 14 without removing patient from patient space 46.

Canopy 24 can additionally be provided with a canopy-mounted accessory 162 mounted to support 144 as shown in FIGS. 12 and 13. Accessory 162 can be, for example, an optical radiation source accessory that directs visible light toward patient 14 for photo therapy treatment of conditions such as jaundice.

Accessory 162 can include a pivotable connector 192 for connecting to canopy 24 as shown in FIG. 12 or canopy 24 can include a pivotable connector 194 for connecting to accessory 162 as shown in FIG. 13. Pins 195 mounted to canopy are received by openings 197 on support 144, shown best in FIG. 7, and a plug 196, shown in FIG. 12, electrically connects accessory 162 to infant thermal support device 10.

Figure 16:
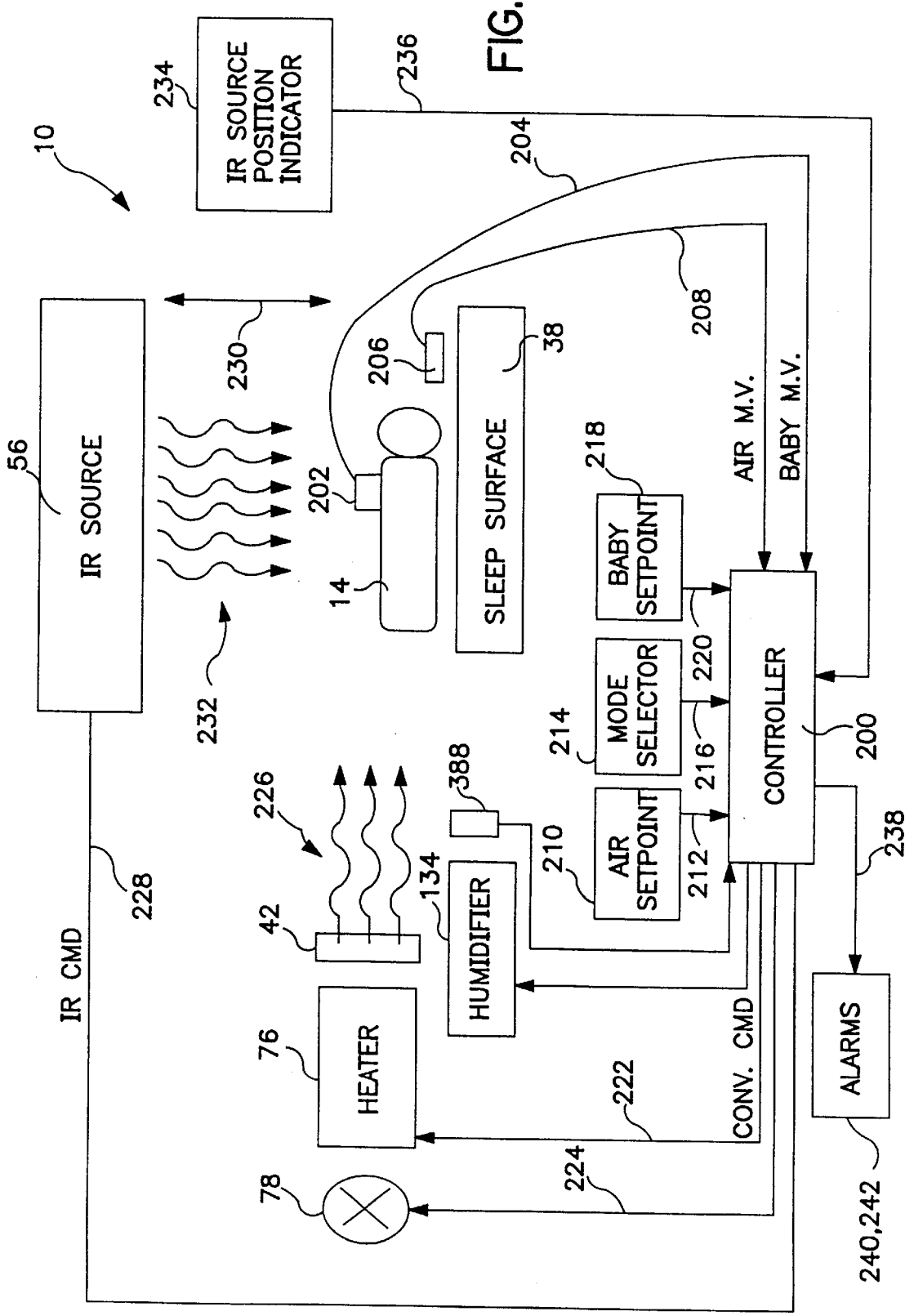
FIG. 16 is a block diagram illustrating a controller for controlling operation of a convective heater and a radiant heater to warm the infant on the sleep surface.

Accessory 162 mounts above x-ray window 178 and above exhaust opening 44 and connectors 192, 194 receive plug 196 of accessory 162. Accessory 162 thus docks to canopy 24, rests on x-ray window 178, and is controlled by controller 200 as shown in FIG. 16. Accessory 162 is rotatable about a pivot axis 198 adjacent to plug 196 as shown in FIGS. 12 and 13 to allow access to x-ray window 178 as shown in FIG. 13 during fluoroscopic procedures. Additionally, accessory 162 can be easily removed and re-installed so that one accessory 162 can be moved between several patient thermal support devices 10.

Patient thermal support device 10 can also be provided with a mattress positioning assembly 180 as shown in FIGS. 14 and 15. In addition, in preferred embodiments, patient thermal support device 10 is provided with weighing capability. Scale load cells 182 are mounted beneath platform 36 and between platform 36 and mattress positioning assembly 180. Load cells 182 provide signals indicating the weight of platform 36 and objects carried by platform 36, including mattress 38 and patient 14, to an output device such as display 160.

Mattress positioning assembly 180 includes scissors-type extenders 184 having a top end coupled to load cells 182 as shown best in FIG. 15. Lead screws 186 are coupled to the bottom ends of extenders 184. Lead screws 186 can be rotated to extend and retract extenders 184 thereby raising and lowering the ends of platform 36 coupled to extenders 184 through load cells 182. Lead screws 186 extend through openings (not shown) in tub 70 and knobs 188 are fixed to lead screws 186 as shown in FIG. 14 to allow the caregiver to rotate lead screws 186 manually.

Platform 36 and consequently patient-support surface 40 of mattress 38 can be adjusted to a Trendelenburg position having patient-support surface 40 tilted at approximately 10 degrees with the head end of patient-support surface 40 lower than the foot end of patient-support surface 40. Patient-support surface 40 can also be moved to a reverse Trendelenburg position having patient-support surface 40 tilted at approximately 10 degrees with the foot end of patient-support surface 40 lower than the head end of patient-support surface 40. In addition, platform 36 can be raised and lowered between an upward position having patient-support surface 40 above vents 42 to facilitate procedures such as intubation of patient 14 and downwardly beneath vents 42 so that if overlays (not shown) are placed on top of mattress 38 resulting in a greater effective mattress thickness, mattress 38 and the overlays can be moved so that the sleeping surface on top of both mattress 38 and the overlays is at the desired height relative to vents 42.

Platform 36 can additionally be formed to include a slot 190 for receiving tray 193 beneath platform 36 as shown in FIGS. 14 and 15. Tray 193 can be used, for example, to carry equipment such as an x-ray cassette 197 for fluoroscopic procedures. As described above, accessory 162 is rotatable about pivot axis 198 to expose x-ray window 178 during fluoroscopic procedures. Mattress 38 and platform 36 are made from radiolucent materials so that x-ray generating equipment (not shown) can be placed above x-ray window 178 and x-ray cassette 197 holding film can be placed in tray 193 allowing fluoroscopic procedures to be performed on patient 14 while patient 14 remains on patient-support surface 40.

FIG. 16 illustrates a control system for the infant thermal support device 10. FIG. 16 illustrates the infant support portion or sleep surface 38, a convection heater 76, a radiant heater 56, a humidifier 134, and a controller 200. The sleep surface 38 is designed to support an infant or baby 14 in such a position so that either the convection heater 76 or the radiant heater 56 can heat the baby 14 as discussed above. The baby 14 can also be warmed by a combination of the convection heater 76 and radiant heater 56. The convection heater 76 and the radiant heater 56 can be used to warm the baby 14 either directly or indirectly. Although the terms "baby" and "infant" are used in this specification, is understood that any patient can use the present apparatus of the present invention, not just a baby or infant.

Controller 200 is a microprocessor based controller having an internal memory. The controller 200 receives various inputs. A baby temperature probe or sensor 202 is attached to the baby 14 to provide a measured baby temperature output signal to the controller 200 on line 204. In addition, an air temperature probe or sensor 206 is positioned near the baby 14 to provide a measured air temperature output signal. The air temperature sensor 206 is connected to the controller 200 by ine 208.

An air temperature set point input device 210 is coupled to controller 00 by line 212. The air temperature input device allows a caregiver to set a desired air temperature setpoint. A mode selector 214 is also coupled to controller 200 by line 16. Mode selector 214 permits a caregiver to select between a Baby Mode of operation, an Air Mode of operation, and a Procedure Mode of operation for the device 10 as discussed in detail below. A baby temperature set point input device 218 is coupled to controller 200 by line 220. The baby temperature input device 218 permits a caregiver to select the desired temperature for the baby 14.

An output from controller 200 on line 222 is coupled to convective heater 76. Another output of controller 200 is coupled to fan 78 by line 224. Controller 200 therefore controls heater 76 and fan 78 to supply a correct amount of convective heat to the infant thermal support device 10 to warm the baby 14 as illustrated diagrammatically by arrows 226. Air flow is controlled by a plurality of vents 42. Vents 42 direct air to warm the baby 14 and also direct air to form one or more air curtains to provide a controlled patient space.

Another output of controller 200 on line 228 is coupled to radiant heater 56. Therefore, controller 200 controls the AIR output from radiant heater 56. The position of radiant heater 56 is adjustable in the direction of double-headed arrow 230 relative to sleep surface 38 by adjusting the canopy support arm (not shown). Heater 56 emits infrared radiation as illustrated diagrammatically by arrows 232 to warm the baby 14. The intensity of radiant heater 56 is adjusted by controller 200 depending upon the position of the heater 56 relative to the sleep surface. A potentiometer or other position indicator 234 is provided to generate an output signal indicative of the position of the radiant heater 56 relative to sleep surface 38. An output of position indicator 234 is coupled to controller 200 by line 236. Controller 200 therefore adjusts the output of radiant heater 56 based on the output signal from position indicator 234 on line 236.

An output from controller 200 on line 238 is coupled to an audible alarm 240 and/or an alarm light 242. Alarms 240 and 242 are used to alert a caregiver of various situations as discussed below.

An output from controller 200 also controls or adjusts the humidifier 134 to control the amount of moisture in the air supplied by the convective heater and used to generate the air curtains. As discussed below, a humidity sensor 388 provides an output signal indicative of the detected relative humidity in the air adjacent sleep surface 38. The controller 200 uses the output signal from humidity sensor 388 to control humidifier 134 to maintain the relative humidity at substantially a preselected level. Also as discussed below, an input device is used to permit the caregiver to adjust the preselected humidity level.

Figure 17:
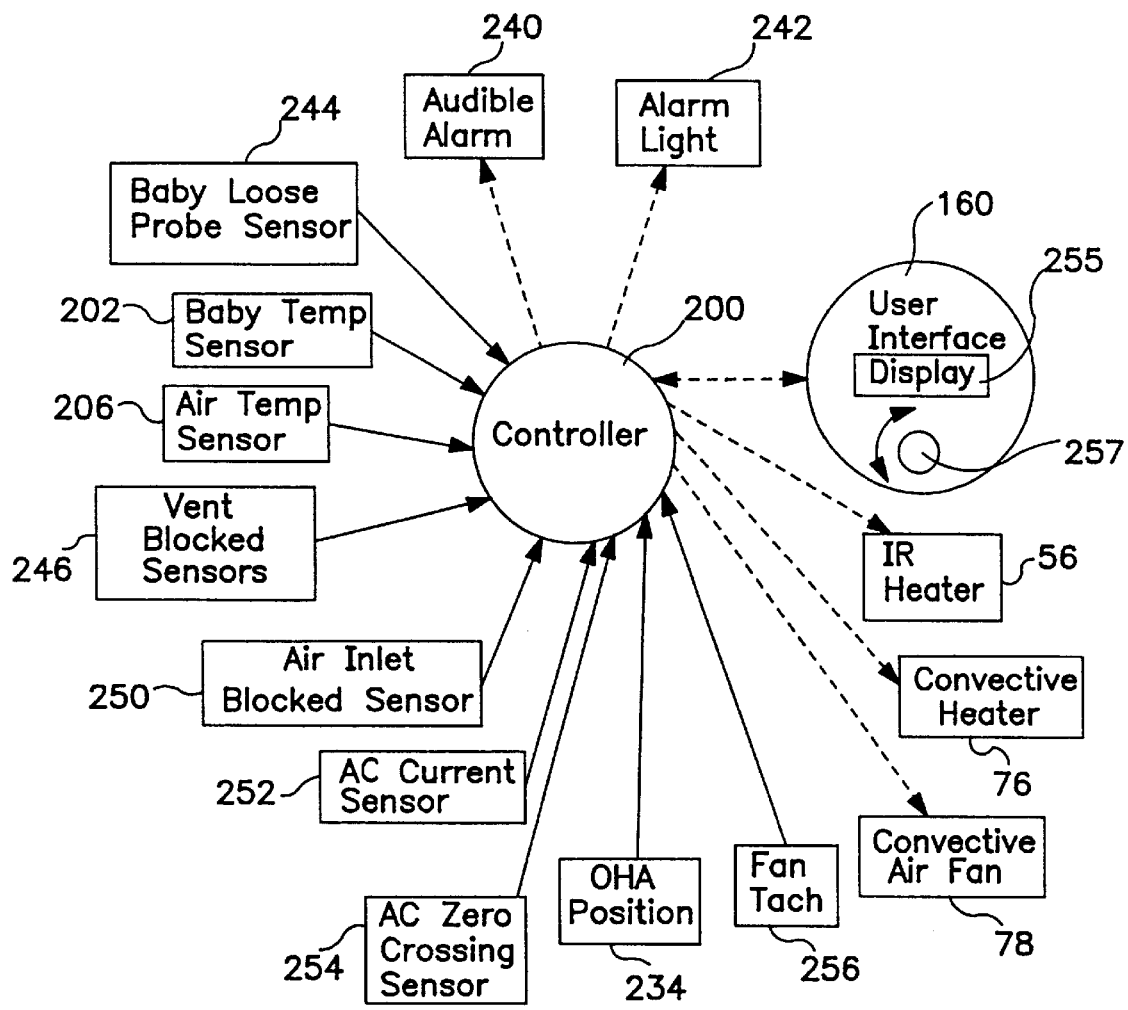
FIG. 17 is a data flow diagram between the controller, a user interface, and the remaining components of the infant thermal support device of the present invention.

FIG. 17 illustrates a data flow block diagram for the controller 200 of the present invention. In addition to the items discussed above, a sensor 244 is provided to indicate that the temperature sensor 202 has come loose from baby 14. A loose probe signal from sensor 244 causes controller 200 to generate an alarm signal on alarms 240 and 242.

In addition, vent blocked sensors 246 are coupled to controller 200.

Sensors 246 illustratively include a right vent blocked sensor, a left vent blocked sensor, a front vent blocked sensor, and a rear vent blocked sensor. An air inlet blocked sensor 250 is also coupled to controller 200. Sensors 246 and 250 provide signals to controller 200 to generate alarms 240 and 242 if the air vents or the air inlet are blocked.

Right vent blocked sensor 246 and left vent blocked sensor 248 detect when air vents adjacent sleep surface 38 are blocked. Sensors 246 and 248 provide an input to controller 200 which generates an output signal on display 255 of user interface of 160 or on alarms 240 or 242. In the preferred embodiment, a pair of sensors are co-located on a narrow material with a low thermal conductivity. For instance, sensors 246 and 248 may be a pair of silicon temperature sensors placed on a thin Kapton ribbon. One of the sensors is operated at a low power level. The other is operated at a moderately high power level, resulting in self-heating of the semi-conductor die and thus an increased temperature indication from the sensor. Air flowing through the vents and across the sensor removes heat and therefore lowers the effective temperature indication. The higher the airflow rate, the more heat is removed. The airflow rate is inversely proportional to the difference of the readings from the two sensors. Therefore, when the temperature difference rises above a predetermined level, an output signal is generated by controller 200 to initiate alarm 240 or alarm 242 or to provide an indication on display 255.

An AC current sensor 252 is also coupled to controller 200. In addition, an AC zero crossing sensor 254 is coupled to controller 200. Sensors 252 and 254 permit controller 200 to monitor current before and after the device 10 is turned on. During an "off" period, controller 200 detects whether the heaters actually turn off The zero crossing sensor 254 checks operation of current sensor 252 and resets the system if no signal is present. A fan tachometer 256 is coupled to controller 200. Fan tachometer 256 provides an input signal to controller 200 indicative of the fan speed. Controller 200 compares the actual fan speed from fan tachometer 256 to the desired fan speed and adjusts a fan command signal to fan 78 accordingly.

A user interface 160 permits the caregiver to input information into controller 200. The user interface 160 may be separate input devices such as devices 210, 214, and 218. The user interface 160 permits the caregiver to input information to controller 200 related to the operation mode, the air temperature set point, the baby temperature set point, a real time clock, and an alarm silencer. Illustratively, a rotatable control wheel 257 is used to scroll through various menu control options. It is understood that any type of control input device may be used. Controller 200 outputs information related to an alarm code, air temperature, and baby temperature to the user interface 160. User interface 160 includes a display 255 so that control information can be displayed to the caregiver.

The communication between controller 200 and user interface 160 is implemented by a serial interface using a master-slave protocol. The controller 200 is the master, and the user interface 160 is slave. Controller 200 controls a communication link by initiating the message transfer. The controller 200 generates a start condition, the user interface address, the read/write bit indicating whether the message is a transmission to the user interface 160 (write) or a request for a message from the user interface 160 (read). Controller 200 also generates a stop condition which indicates the end of a message. The user interface 160 responds only when a transfer has been initiated by the master controller 200. It is understood that other communication protocols may be used in accordance with the present invention.

The controller 200 of the present invention has three operating modes for controlling warming of the baby 14. These operation modes are a Baby Mode, an Air Mode and a Procedure Mode. In the Air Mode, chamber air is under servo-control. The control point is the air setpoint. The infrared energy source is disabled during Air Mode. In the Baby Mode, the controller 200 combines convective heat and infrared energy to servo-control about the baby temperature setpoint. In the Procedure Mode, infrared energy is supplied at a level set by the caregiver. Chamber air is warmed to a preset level using the convective heater.

In this specification, the term "air setpoint" is a control point temperature for Air Mode. The "baby setpoint" is a control point temperature for Baby Mode. "Measured air temperature" is a calibrated temperature measurement of the ambient air by sensor 206 in the vicinity of the sleep surface 38. "Measured baby temperature" is a calibrated temperature measurement of the probe 202 on the baby. "Overhead arm condition" is an indication of the relative position of the overhead arm supporting radiant heater 56 from position indicator 234. "Convective command" is a value that represents the percent convective heater power. "AIR command" is a value that represents the desired power density at the mattress surface. "Stability" or "stable" is when temperature fluctuations of less than 0.3° C. are observed, and these fluctuations are predominately centered about the setpoint.

When power to the device 10 is turned on, two possible states are defined, distinguished by the amount of time that the device 10 has been shut off. A warm-start is initiated if the device has been off for less than 10 minutes. The operating mode, setpoints and other conditions in effect prior to the power loss are restored. Controller 200 then resumes control functions, in the state that it was just prior to the removal of power. The device also includes a Prewarm Mode (Cold-Start). The Prewarm Mode is initiated by controller 200 automatically if the power on occurs more than 10 minutes from the last use of the device. This prewarm mode is intended to assist caregivers in preparing the device for use. The functionality of the prewarm "mode" is that of air-mode with the air setpoint at a default value (e.g. 35° C.). An air mode icon will be illuminated on the display, baby mode and procedure mode icons will be extinguished. The message "prewarm" will be indicated on the LCD display screen. Under temperature alarms are inactive in Prewarm mode. Alarms related to system errors (e.g. system failure, heater fault, etc.) are active. When the temperature has reached the Prewarm temperature and has been stable for 2 minutes, the message "Ready for Use—Select Operating Mode" appears on the LCD screen. This message stays on the LCD screen until the mode is canceled. The Prewarm mode is canceled by deliberate action from the caregiver. This can come at any time during the Prewarm mode. Pressing the mode, increment or decrement keys, will initiate an exit from Prewarm mode.

In Air Mode, the air temperature inside the infant receiving space is controlled using only the convective heater 76 and fan 78. The controller 200 adjusts the convective heater 76 to maintain the desired air temperature. In the Air Mode, the radiant heater 56 is off. The baby probe 202 is not needed for operation in the Air Mode. If, however, the probe 202 is connected to the device, then the measured baby temperature is displayed. The baby temperature setpoint is not used in Air Mode. An air icon is illuminated, and Baby Mode and Procedure Mode icons are extinguished. Alarms related to system errors (e.g. system failure, heater fault, etc.) are active.

An "overtemperature condition" exists when the air temperature measured by sensor 206 exceeds the air setpoint by more than 1° C. Over-temperature alarms are always active. An "undertemperature condition" exists when the air temperature measured by sensor 206 is less than the air setpoint by more than 1° C. Undertemperature alarms are active after an undertemperature hold-off period. When the air setpoint is increased, the undertemperature alarm is defeated until the air temperature has risen and stabilized about the new setpoint. After the air temperature has been stable for two minutes at the new setpoint, then undertemperature alarm is reactivated.

A setpoint error ($E_{sp}$) is continuously calculated by the controller 200 from the difference of the air setpoint ($SP_{air}$) and the air temperature measured value as follows:

$$E_{sp} = SP_{air} - MV_{air}$$

Where:
  $SP_{air}$ is air temperature setpoint.
  $MV_{air}$ is the measured value of the air temperature by sensor 206.

Controller 200 operates to drive $E_{sp}$ to zero. This is accomplished with "three term" control, providing Proportional (P), Integral (I) and Derivative (D) responses, calculated from the present and recent values of $E_{sp}$. The individual responses are summed, forming the input to a power output block (the term block is used here to represent a function or group of functions). The power block receives the PID sum and produces an output command which represents the required amount of heater power to drive $E_{sp}$ toward zero.

Figure 18:
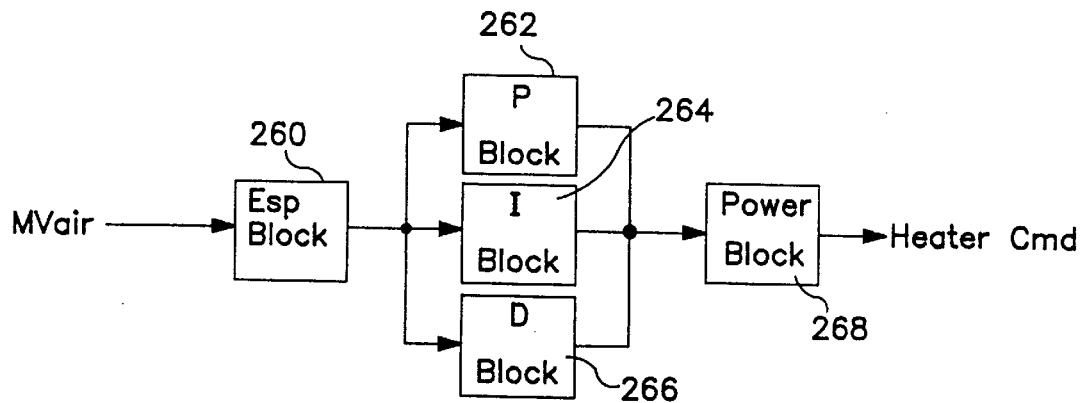
FIG. 18 is a control block diagram for an Air Mode of operation of the present invention.

A block diagram of Air Mode control is illustrated in FIG. 18. The $E_{sp}$ block 260 calculates $E_{sp}$ as discussed above. The P Block 262 in FIG. 18 produces the proportional term which increases with the magnitude of $E_{sp}$, has the same algebraic sign as $E_{sp}$, and is zero when $E_{sp}$ is zero. Calculation of the P term is as follows:

$$P = K_p \cdot E_{sp}$$

Where:
$K_p$ is a proportional gain constant.

The I Block 264 in FIG. 18 produces the integral term which is created from calculation of the area of the curve of $E_{sp}$ vs. time. With constant error, I ramps. When the error is zero, I remains unchanged. An appropriate numerical method (for example the trapezoidal rule) can be used to compute the integral term. The I term is calculated as follows:

$$I = K_i \cdot \int E_{sp} dt$$

Where:
t is time
$K_i$ is an integral gain term.

The D Block 266 of FIG. 18 produces the derivative term which is created from calculation of the rate of change $E_{sp}$. With constant error, D is zero. The D term is calculated as follows:

$$D = K_d \cdot \frac{dEsp}{dt}$$

Where:
$K_d$ is a derivative gain term.

P, I and D are added together and presented to the power block 268. The power block translates this sum into a heater command to control convective heater 76. Prior to summation the P, I & D terms are bounded to assure that the heater response is constrained to reasonable values.

Constraint on P: $-P_{max} < P < P_{max}$
Constraint on I: $-I_{max} < I < I_{max}$
Constraint on D: $-D_{max} < D < D_{max}$ Where:
$P_{max}$ is the Lower/Upper limit for P.
$I_{max}$ is the Lower/Upper limit for I.
$D_{max}$ is the Lower/Upper limit for D.

The equation for heater power command is as follows:

$$H_{cmd} = (P+I+D) \cdot K_{htr}$$

Figure 19:
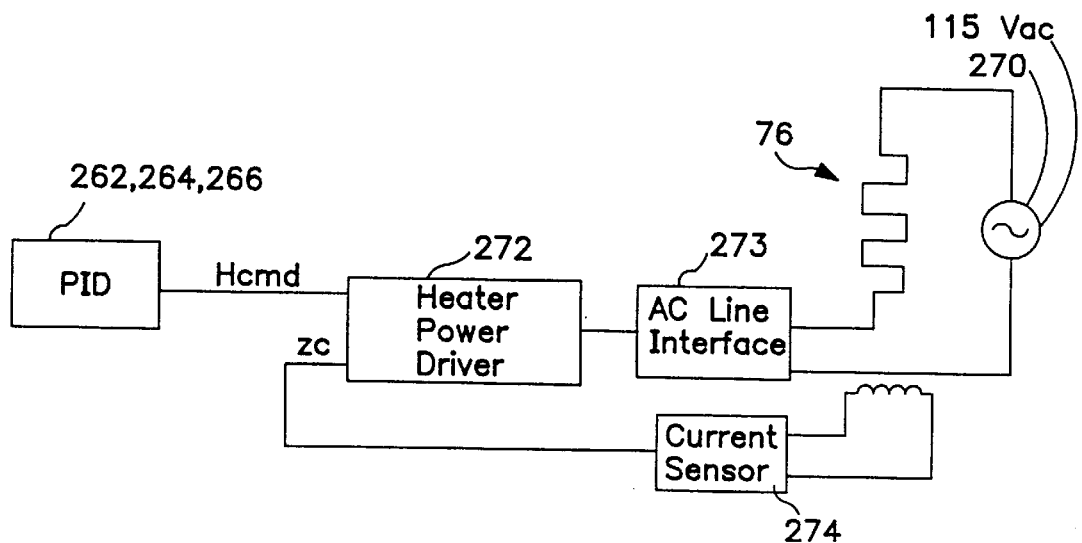
FIG. 19 is a block diagram of a heater control circuit.

Where:
P, I and D are the bound values of above equations.
$K_{htr}$ is a heater gain constant A function, the heater power driver, provides power to the heater 76. The input to this function is $H_{cmd}$, which is periodically updated by the PID action. A block diagram of the heater circuit is illustrated in FIG. 19. The heater load 76 is driven from an AC line 270, and is modulated with a time proportioning algorithm. At any given time, the heater 76 is either on or off. Variable power levels are achieved by modulating the on/off characteristic of heater 76. The minimum on time is one-half of the AC line period (e.g. 8.3/10.0 ms with 60/50 Hz mains). The integration period is 100 such half-line cycles. The integration period is chosen so that the time constant of the heater is much greater than integration period. 40% power, for example, is achieved by turning the heater full on for 40 half-cycles and off for 60 half-cycles. At the end of an integration period, a new $H_{cmd}$ is received and a new on/off characteristic is created for the new value of $H_{cmd}$. $H_{cmd}$ signals are created in the PID function block 262, 264, 266 and made available to the heater power driver 272. These two functions operate asynchronously. $H_{cmd}$ is transferred via a mailbox. An AC line interface 273 is coupled between heater power driver 272 and heater 76.

An example output is:
1. Turn on the heater at the start of an integration cycle.
2. Keep it on for the requested power level.
3. Turn the heater off and wait for the integration period to be done.

Power limiting may be desired to keep from exceeding the maximum power draw. A current sensor 274 on the AC lines are available for this.

Figure 20:
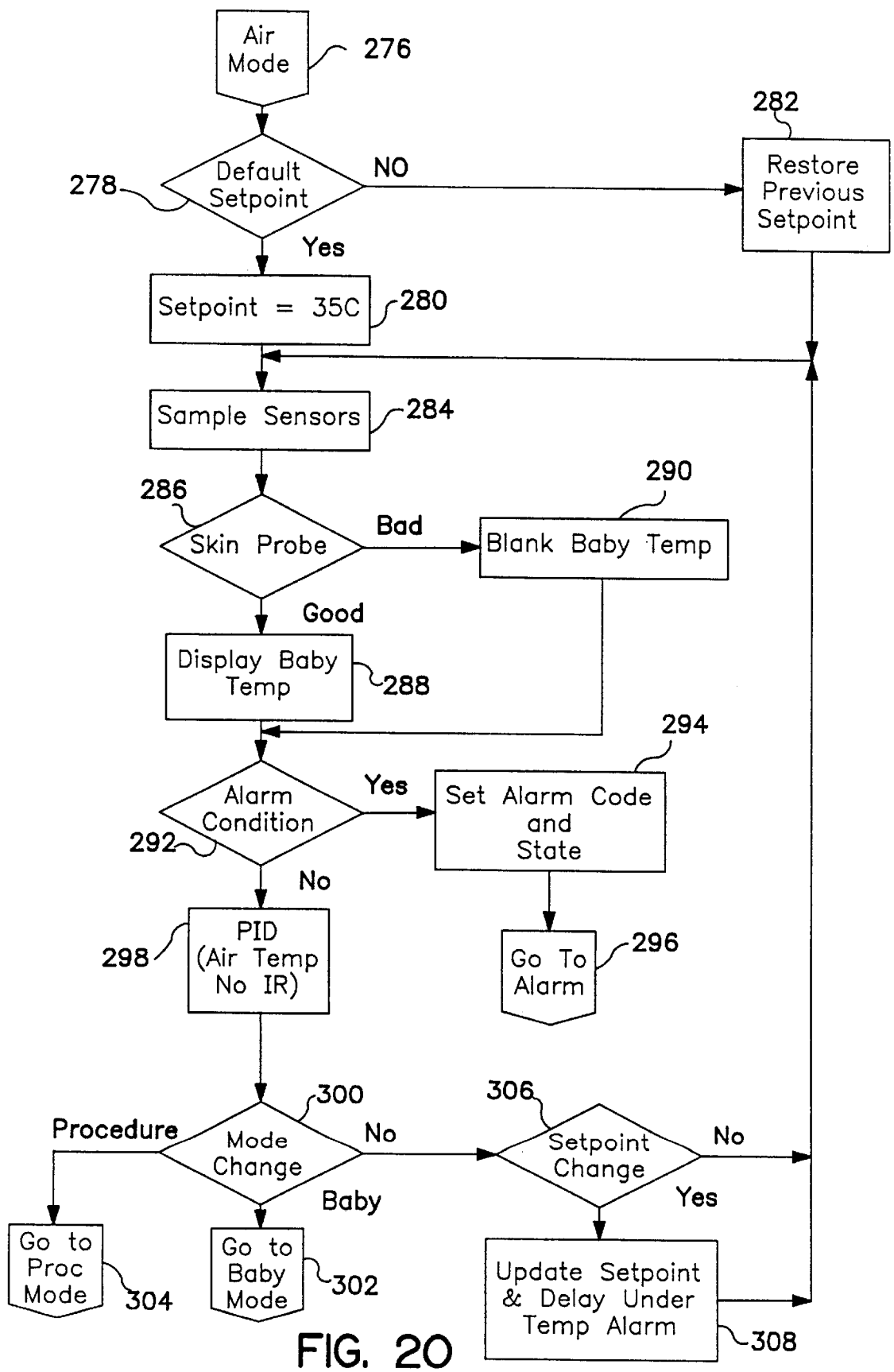
FIG. 20 is a flow chart illustrating the steps performed by the controller during an Air Mode of operation.

FIG. 20 illustrates the steps performed by the controller 200 during the Air Mode of operation. The Air Mode is initiated as illustrated as block 276. Controller 200 determines whether to use the default temperature setpoint at block 278. If the default is to be used, the air temperature setpoint is set at 35° C. as illustrated at block 280. If the default setpoint is not to be used at block 278, controller 200 restores the previous setpoint established by air temperature setpoint input device 210. This step is illustrated at block 282. Once the previous setpoint is restored at block 282, controller advances to block 284 and samples sensors 202 and 206. Controller 200 determines whether the skin probe 202 is connected at block 286. If so, controller 200 display the baby temperature on the display as illustrated at block 288. If the baby temperature sensor 202 is not connected, controller 200 blanks the baby temperature display as illustrated at block 290.

Controller 200 next determines whether an alarm condition exists as illustrated at block 292. If so, the controller 200 sets the alarm code at block 294 and sounds the appropriate alarm 240 or 242 as illustrated at block 296. If an alarm condition does not exist at block 292, the controller 200 uses the PID control discussed above to control the air temperature of the device as illustrated at block 298. Controller 200 then determines whether a mode change has been made on mode selector input 214 at block 300. If a mode change has occurred, controller 200 moves to either the Baby Mode as illustrated at block 302 or the Procedure Mode as illustrated at block 304.

If a mode change has not occurred at block 300, controller 200 determines whether the air temperature setpoint has been changed at block 206. If not, the controller advances back to block 284. If the air temperature setpoint has been changed at block 306, controller 200 updates the setpoint temperature and initiates the delay for the under temperature alarm as discussed above as illustrated at block 308. Controller 200 then advances back to block 284.

In the Baby Mode, controller 200 makes the full use of both heater systems, applying convective heat from heater 76 and also applying radiant warming from heater 56 as needed to maintain the skin temperature of the baby 14 at the baby temperature setpoint. Baby Mode requires that the skin probe 202 is connected to the baby 14. In Baby Mode, the air temperature is displayed, but the air temperature setpoint is not used. A baby icon is illuminated on the display, and the Air and Procedure mode icons are extinguished. An overtemperature condition exists when the baby temperature exceeds the baby temperature setpoint by more than 0.5° C. Overtemperature alarms are always active. An undertemperature alarm exists when the air temperature is less than the baby temperature setpoint by more than 0.5° C. Undertemperature alarms are active after the undertemperature hold-off period. See the discussion in the preceding section (Air Mode) for a definition of undertemperature hold-off.

The setpoint error ($E_{sp}$) for Baby Mode is continuously calculated from the difference of the baby setpoint ($SP_{baby}$) and the baby temperature measured value as follows:

$$E_{sp} = SP_{baby} - MV_{baby}$$

Where:
$SP_{baby}$ is the Baby temperature setpoint.
$MV_{baby}$ is the measured value of the baby.

Figure 21:
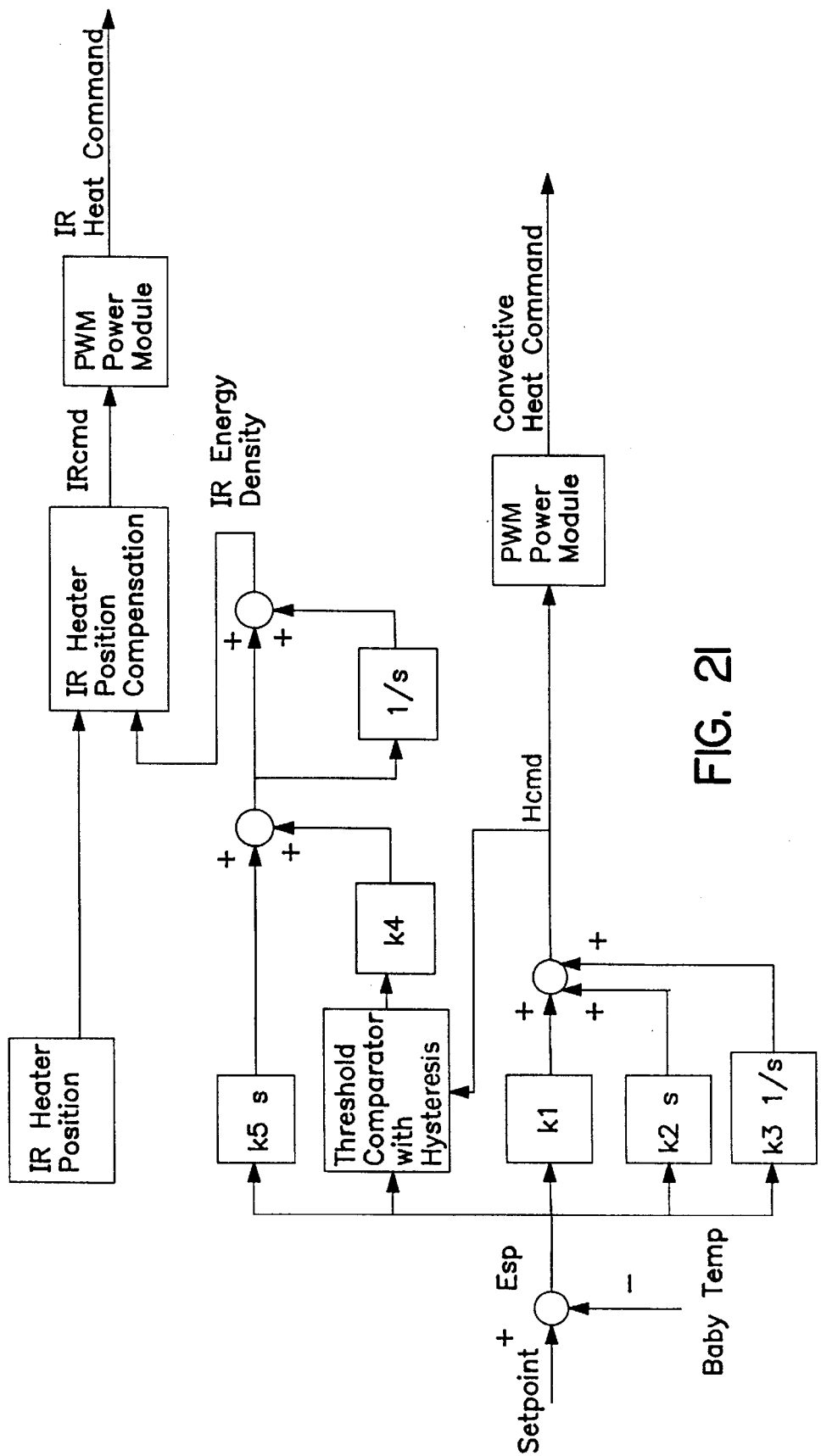
FIG. 21 is a control block diagram of the controller of the present invention.

The convective heater is controlled with the PID control block, as illustrated in FIG. 21. An additional loop, controlling the AIR heater is added when operating in the Baby Mode. AIR heating is basically an "I" only controller. The AIR heating loop derives input from the derivative and heat command ($H_{cmd}$) terms of the convective PID loop.

In FIG. 21, K1 is a convective proportional gain constant. K2 is a convective derivative gain constant. K3 is a convective integral gain constant. K4 is an IR proportional gain constant. K5 is an IR derivative gain constant. The control lock diagram is used to generate both the convective heat command for controlling heater 76 and the IR heat command for controlling the radiant heater 56. Both the heat commands are generated by a pulse width modulation power module. The output of the Threshold Comparator is $E_{sp}$ when $H_{cmd}$ is greater than $H_{ul}$. The output of Threshold Comparator is zero when $H_{cmd}$ is between $H_{ul}$ and $H_{ll}$. The output of Threshold Comparator is $-E_{sp}$ when $H_{cmd}$ is less than $H_{ll}$.

Figure 22:
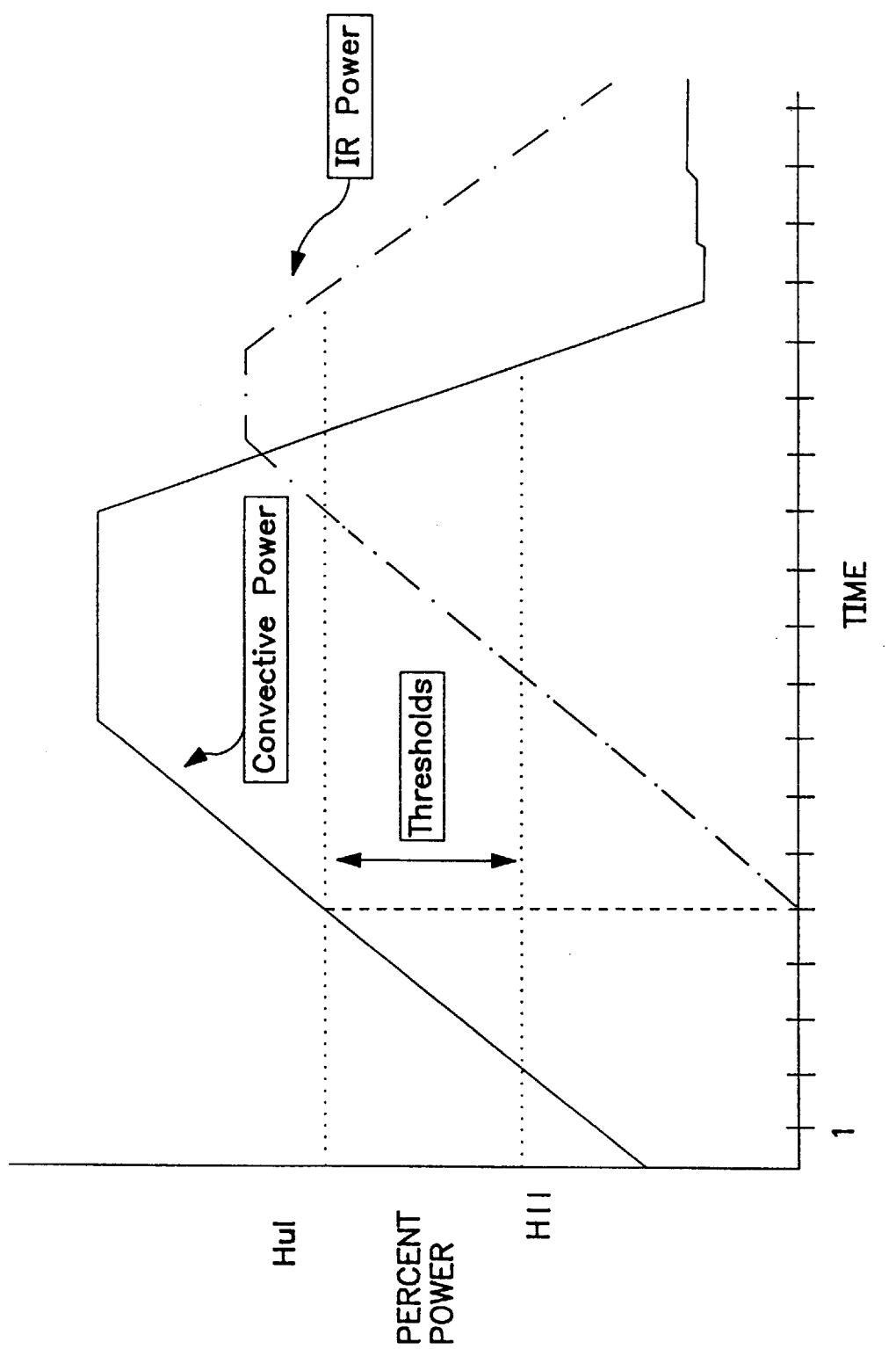
FIG. 22 is a diagrammatic view illustrating control of the convective heater and radiant heater in a Baby Mode of operation.

The derivative term of the convective loop is responsive to the instantaneous rate of change of $E_{sp}$. This provides quick IR heating if the baby measured value ($MV_{baby}$) drops. The $H_{cmd}$ term of the convective loop represents power applied to the convective heater. When convective power exceeds an upper threshold ($H_{ul}$), IR energy begins to ramp up. This continues while the convective power is above $H_{ul}$. When the convective power falls below a lower threshold ($H_{ll}$, the IR energy begins to ramp down. This is illustrated in FIG. 22.

$$IR_{ed(k)} = IR_{ed(k-1)} + \left(K_{ird} \cdot \frac{dE_{sp}}{dt} + SGN \cdot K_{irp}\right) \cdot UR$$

Where:
$IR_{ed(k)}$ and $IR_{ed(k-1)}$ are IR energy densities (e.g. mW/cm$^2$).
$K_{ird}$ is an IR gain constant for the derivative term.
$K_{irp}$ is an IR gain constant for the proportional term.
UR is an update rate of $IR_{ed}$.
SGN is +1 when $H_{cmd} > H_{ul}$, -1 when $H_{cmd} < H_{ll}$, and 0 otherwise.

Energy density varies inversely with the distance of the IR heater 56 from the sleep surface 38. Wide variations in energy density (at the sleep surface 38) will be observed for a given power level as the radiant heater is moved up and down. To overcome this, the power level is adjusted as a function of the overhead arm height. A position indicator 234 such as a potentiometer is connected to the arm lift mechanism provides position output signal to controller 200. The potentiometer voltage is periodically monitored by the controller 200 and used in the heater control function. The potentiometer voltage ranges from $V_{posl}$ to $V_{posh}$, and varies directly with position. The relative position is given by:

$$OHA_{rel} = \frac{\Delta V}{Span} = \frac{Vpos - Vposl}{Vposh - Vposl} \cdot 100\%$$

Where:
$V_{pos}$ is the Position Sensor 234 A/D value.
$V_{posl}$ is a Lower limit on the position A/D value.
$V_{posh}$ is an Upper limit on the position A/D value.
$OHA_{rel}$ is the Overhead arm relative position.

The absolute position of the IR sources with respect to the mattress surface is:

$$OHA_{abs} = OHA_{rel} + OHA_{min}$$

Where:
$OHA_{rel}$ is the Relative position of the Overhead Arm.
$OHA_{min}$ is the Position of the Overhead Arm when "full down".

To achieve a relatively constant energy density on the mattress surface 38, the following equation is used:

$$IR_{ed} = \frac{1}{K_{ir} \cdot OHA_{abs}^n} \cdot IR_{cmd}$$

Where:
$IR_{ed}$ is the Energy Density at the mattress surface.
$K_{ir}$ is a constant.
$OHA_{abs}$ is the absolute position of the IR sources wrt to the mattress surface as given in the above equation.
n is a constant.
$IR_{cmd}$ is the duty cycle of the IR heater 56.

This constant energy density equation can be re-arranged to yield the IR source duty cycle as a function of Energy Density.

$$IR_{cmd} = IR_{ed} \cdot K_{ir} \cdot OHA_{abs}^n$$

Modifiers to the control algorithm are necessary to accommodate special conditions. The power command to the heater must be modifiable based on the state of various alarms and system failures. For example if a system failure were to occur, the heater should be commanded to zero power. Power limiting may be necessary to keep from exceeding the maximum power draw. Current sensors on the AC lines are available for this.

Figure 23:
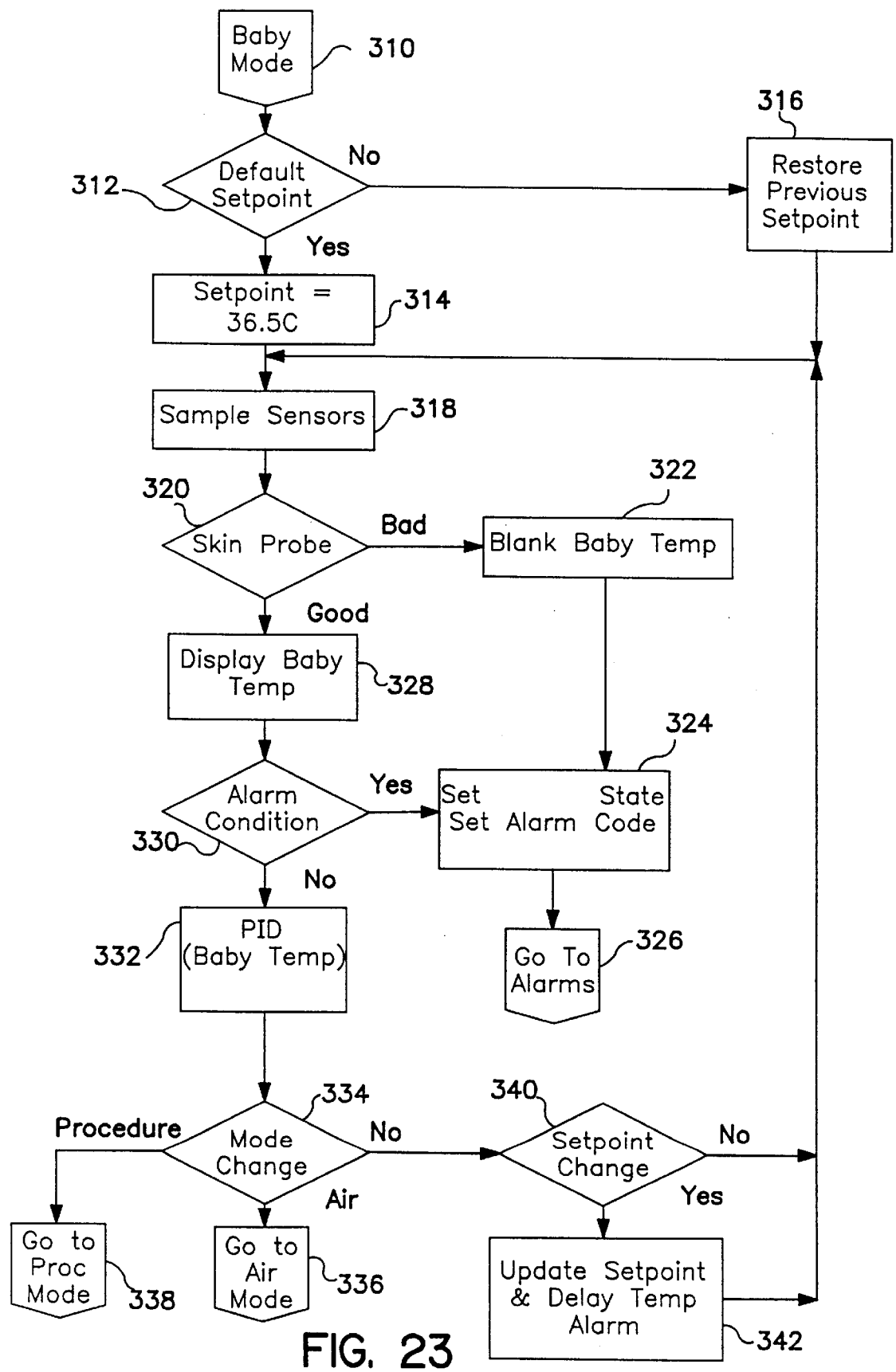
FIG. 23 is a flow chart illustrating the steps performed by the controller during the Baby Mode of operation.

Operation of the controller 200 in the Baby Mode is illustrated in FIG. 23. The Baby Mode begins at block 310. Controller 200 determines whether the use the default baby temperature setpoint as illustrated at block 312. If the default baby temperature setpoint is to be used, controller 200 sets the baby temperature setpoint at 36.5° C. as illustrated at block 314. If the default setpoint is not used, the controller 200 restores the previous baby temperature setpoint input on the baby temperature setpoint input device 218 as illustrated at block 316. The controller 200 then advances to block 318 and samples the output signals from sensors 202 and 206. Controller 200 determines whether skin probe sensor 202 is working or attached at block 320. If not, controller 200 blanks the baby temperature output on the display as illustrated at block 322. Controller then sets an acceptable state and sets an alarm code at block 324. An appropriate alarm 240 or 242 is activated to indicate that the baby sensor 202 is unattached or not functioning as illustrated at block 326. If the baby temperature sensor 202 is functioning properly, controller 200 displays the baby temperature at block 328.

Controller 200 determines whether an alarm condition has occurred at block 330. If so, controller 200 advances to blocks 324 and 326. If an alarm condition has not occurred, controller 200 controls the convective heater 76 and radiant heater 56 using the PID control discussed above as illustrated at block 332.

Controller 200 then determines whether a mode change has occurred at block 334. If so, the controller 200 moves to the Air Mode as illustrated at block 336 or the Procedure Mode as illustrated at block 338.

If the mode is not chanced at block 334, controller 200 determines whether the baby temperature setpoint has been changed at block 340. If not, controller 200 advances to block 318. If the baby temperature setpoint has changed at block 340, controller 200 updates the baby temperature setpoint and delays the temperature alarm as illustrated at block 342. Controller 200 then advances to block 318.

Procedure mode is similar to the manual mode of radiant warmers. Caregivers can adjust the IR energy as required by the procedure. The skin probe 202 need not be connected in this mode. If it is, the skin temperature will be displayed. If it is not, the skin temperature on the display will be blanked.

The air temperature is displayed, but the air temperature setpoint is extinguished. The procedure icon is illuminated, and the air and baby icons are extinguished. IR energy density is set by the caregiver. The IR source duty cycle is modulated as a function of the overhead arm distance, as described above. The convective energy is supplied at a specified level.

Figure 24:
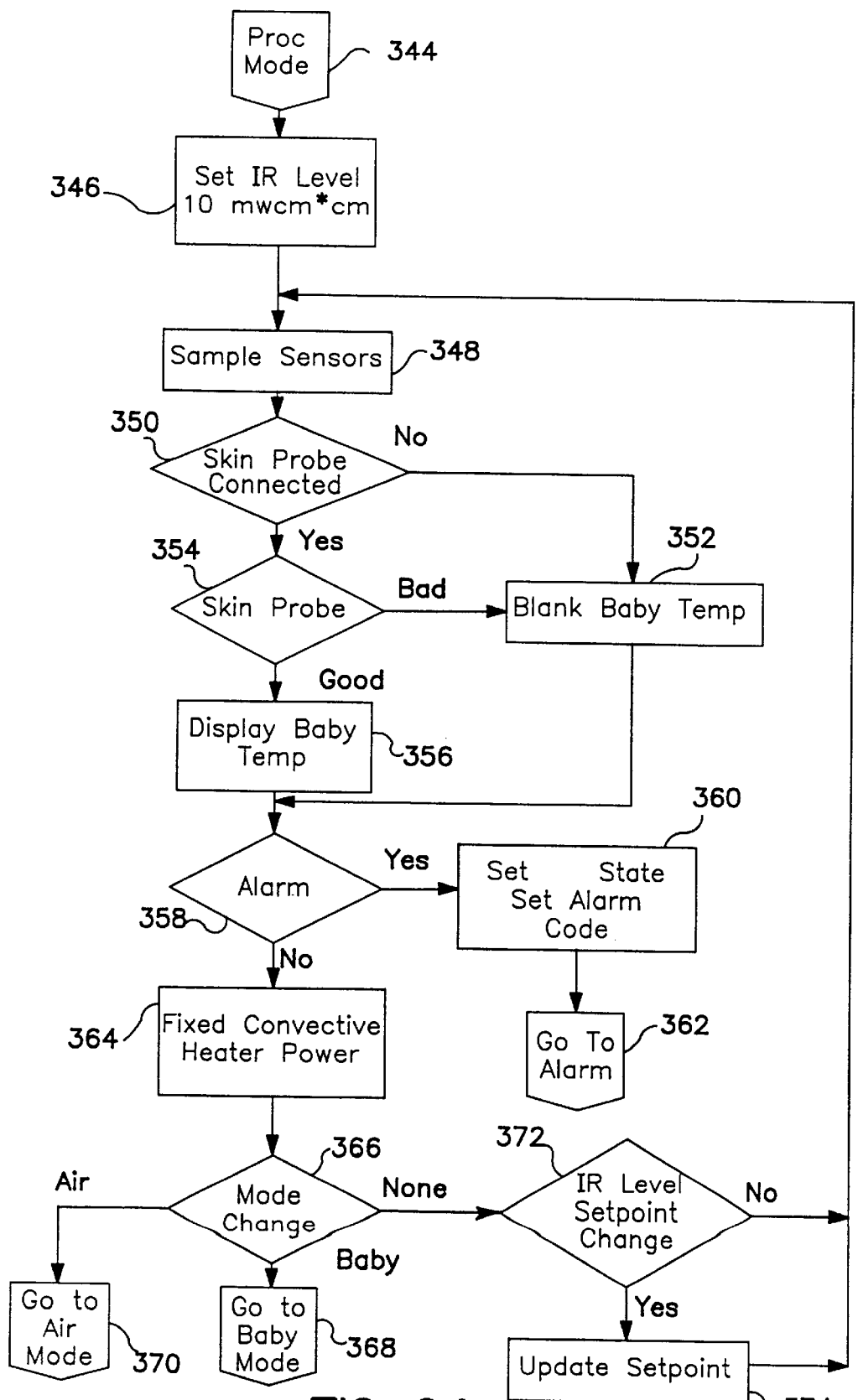
FIG. 24 is a flow chart illustrating the steps performed by the controller of the present invention during a Procedure Mode of operation.

The operation of controller 200 in the Procedure Mode is illustrated in FIG. 24. The Procedure Mode begins at block 344. Controller 200 sets the IR level at 10 mW/cm$^2$ as illustrated at block 346. Controller 200 samples sensors 202 and 206 as illustrated at block 348. Controller 200 determines whether the baby skin probe is connected at block 350. If not, controller 200 blanks the baby temperature output to the display as illustrated at block 352. Controller 200 then advances to block 358. If the skin probe is connected at block 350, controller determines whether the output from the skin probe is a valid reading at block 354. If not, controller 200 advances to block 352. If the sensor 202 reading is valid, controller 200 display the baby temperature at block 356.

Controller 200 determines whether an alarm condition is present at block 358. If so, controller 200 sets a acceptable state and sets the alarm code at block 360. Controller 200 then sounds the appropriate alarm 240 or 242 as illustrated at block 362. If an alarm condition is not present at block 358, controller 200 provides a fixed convective heater power as illustrated at block 364. Controller 200 then determines whether a mode change has occurred from mode selector 214 as illustrated at block 366. If a mode change has occurred, controller 200 advances to the Baby Mode as illustrated at block 368 or the Air Mode as illustrated at block 370.

If the mode has not changed at block 366, controller 200 determines whether the IR level setpoint has changed at block 372. If not, controller 200 advances to block 348. If the IR level setpoint has changed at block 372, controller 200 updates this setpoint as illustrated at block 374 and then advances to block 348.

Figure 25:
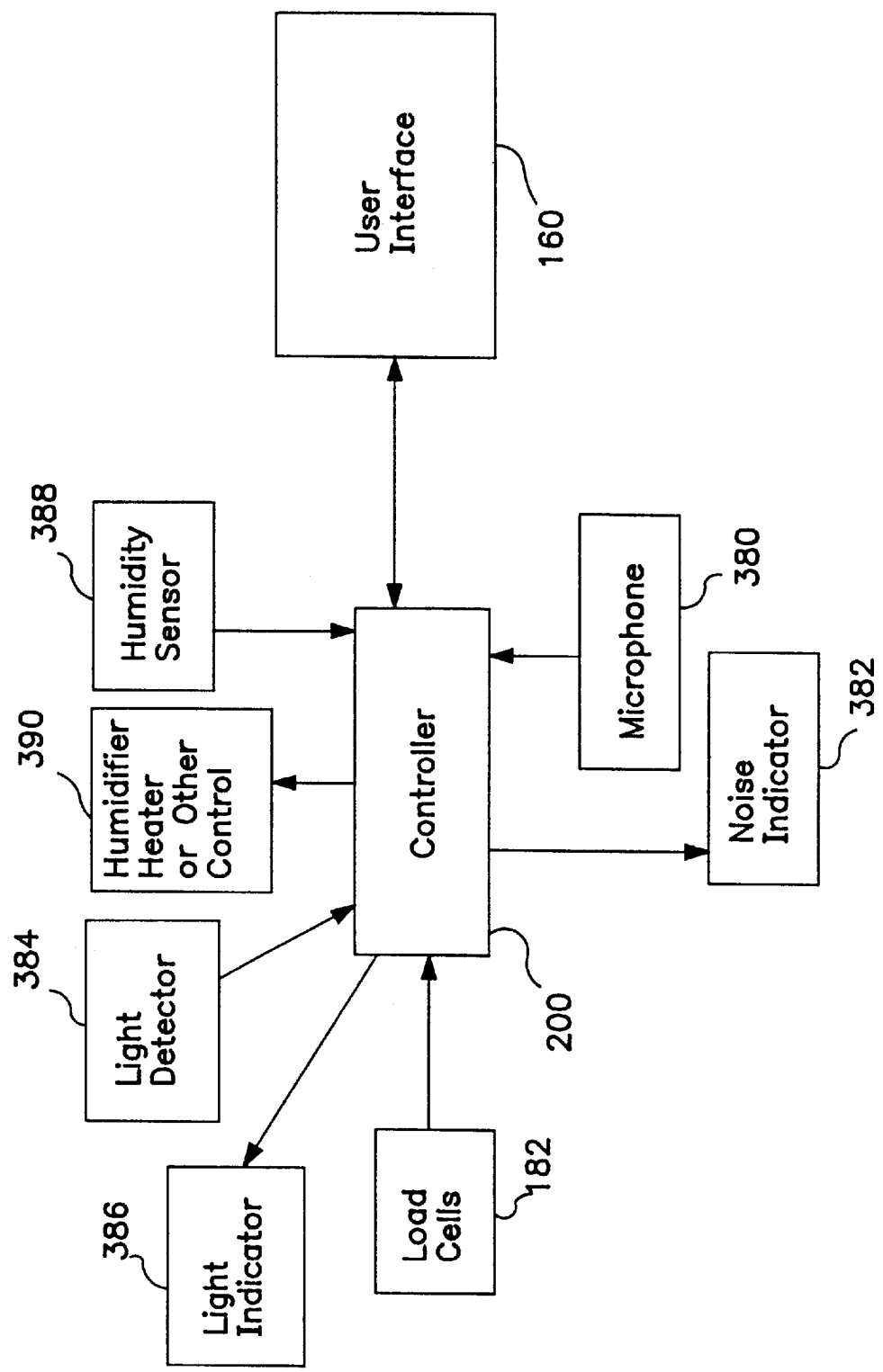
FIG. 25 is a block diagram illustrating additional features of the present invention.

Additional features of the present invention are illustrated in FIG. 25. Another aspect of the present invention is noise monitoring in the region adjacent the device 10. The noise monitor apparatus provides a visual indication using display 255 or alarm light 242 when a predetermined noise threshold has been exceeded. A microphone 380 is located in close proximity to device 10. The microphone 380 may be positioned on the device 10 itself near sleep surface 38. In addition, microphone 380 may be placed on the baby 14 along with temperature sensor 202. The microphone provides an output signal to controller 200 to indicate the noise level. A caregiver can set a predetermined threshold level using a control on user interface 160. If the predetermined threshold noise level is exceeded, controller 200 generates an output signal to initiate the noise indicator 382.

Controller 200 is also coupled to a light detector 384. Again, light detector 384 can be located anywhere adjacent device 10. Preferably, light detector 384 is located near sleep surface 38. Light detector 384 may be coupled to the baby 14 adjacent temperature sensor 202. The caregiver can provide a predetermined threshold light level using user interface device 160. Controller 200 provides an output signal to a light indicator 386 indicating that the preselected light level has been exceeded. A display 255 on the user interface 160 can be used for the light indicator.

Controller 200 can store the signals from microphone 380 and light detector 384 if desired. These stored signals can be processed and displayed to the caregiver. The noise indicator 382 and light indicator 386 may be coupled to the device 10 or located at a remote location.

Controller 200 is also coupled to an output from load cells 182. Controller 200 processes the signals from load cells 182 to provide an indication of the weight of the patient. The output may be displayed on display 255 of user interface 160. A caregiver can provide an input for a weight request or tare weight request to the scale using controls on user interface 160. Controller 200 then measures the weight and provides the weight indication signal to user interface 160. If desired, the weight signal can be transmitted to remote location. The scale works even when the sleep surface 38 is aligned at an angled orientation.

The device 10 also includes a humidity sensor 388 for detecting relative humidity. Typically, a humidifier 134 for the patient thermal support device 10 includes an evaporator tray which is heated by a heater to supply water vapor to an air stream. In the present invention, a caregiver can control the desired relative humidity in the air moving through the device 10. Controller 200 detects the humidity level from sensor 388 and compares it to the preset humidity level set by the caregiver or automatically by the controller to a default level. Controller 200 sends an output signal to a humidifier heater or other humidifier control as illustrated at block 390. For instance, if it is desired to increase the humidity, the humidifier heater temperature is increased to increase the level of water vapor in the air. Controller 200 generates output signals to user interface 160 indicating that the humidifier is present, indicating the percent relative humidity, or indicating that the humidifier evaporation tray is out of water. A caregiver can use the user interface 160 to turn on the humidifier and to set the preselected humidity level.

Although a PID controller is disclosed in the illustrated embodiment, it is understood that a controller using another type of control system or technique may be used to control the convective heater 76, the radiant heater 56, and the humidifier 134 in accordance with the present invention. For example, proportional control, adaptive control, fuzzy logic control, or neural network control can be used for controller 200, if desired.

Although the invention has been described with reference to preferred embodiments, additional variations and modifications exist within the scope and spirit of the invention as described and defined in the following claims.

What is claimed is:

1. A patient warming apparatus, comprising:
   a) a patient support surface;
   b) a convective heater;
   c) an assembly comprising a canopy and a radiant heater, the assembly being movable upwardly and downwardly relative to the support surface between a lower position and an upper position; and
   d) a controller having a first output coupled to the convective heater and a second output coupled to the radiant heater, the controller operating to energize the radiant heater when the assembly is in the upper position, and to de-energize the radiant heater and energize the convective heater when the assembly is in the lower position.

2. Apparatus according to claim 1, further comprising a position indicator having an output and being configured to generate an output signal indicative of the position of the assembly.

3. Apparatus according to claim 2, wherein said output of the position indicator is coupled to the controller.

4. Apparatus according to claim 1, further comprising a humidifier for adding moisture to air adjacent the support surface.

5. Apparatus according to claim 4, wherein said controller has an output coupled to the humidifier.

6. Apparatus according to claim 1, further comprising a fan, and wherein said controller has an output coupled to the fan.

7. Apparatus according to claim 6, wherein the fan is energized by the controller when the assembly is in the lower position.

8. Apparatus according to claim 1, further comprising an air temperature sensor having an output and being configured to produce a signal indicative of air temperature in the apparatus.

9. Apparatus according to claim 8, wherein the output of the air temperature sensor is coupled to the controller.

10. Apparatus according to claim 1, further comprising a patient temperature sensor having an output and being configured to produce a signal indicative of the temperature of the patient.

11. Apparatus according to claim 10, wherein the output of the patient temperature sensor is coupled to the controller.

12. Apparatus according to claim 1, further comprising a mode selector coupled to the controller and configured to allow a caregiver to operate the apparatus in a selected one of a plurality of modes for controlling warming of the patient.

13. Apparatus according to claim 12, wherein the mode selector allows the caregiver to operate the apparatus in at least a first mode in which the assembly is in the upper position and the radiant heater is energized to warm the patient, and a second mode in which the assembly is in the lower position, the radiant heater is de-energized, and the convective heater is energized to warm the patient.

14. Apparatus according to claim 13, wherein the convective heater and the radiant heater are energized in the first mode to warm the patient.

15. Apparatus according to claim 13, wherein the controller adjusts the convective heater when the apparatus is operating in the second mode to maintain a desired air temperature in the vicinity of the support surface.

16. Apparatus according to claim 12, wherein the mode selector allows the caregiver to operate the apparatus in a mode in which the radiant heater is energized by the controller and supplies infrared energy at a level set by the caregiver to warm the patient.

17. Apparatus according to claim 12, wherein the controller energizes the convective heater and the fan in said mode to provide air warmed to a preset level to the apparatus.

18. A patient warming apparatus, comprising:
   a) a patient support surface;
   b) a convective heater;
   c) an assembly comprising a canopy and a radiant heater, the assembly being movable upwardly and downwardly relative to the support surface between a lower position and an upper position;
   d) the canopy and support providing an enclosure when the assembly is in the lower position cooperating with the convective heater to warm the patient;
   e) the radiant heater providing heat to the patient on the support when the assembly is in the upper position; and
   f) a controller having a first output coupled to the convective heater and a second output coupled to the radiant heater, the controller operating to energize the radiant heater when the assembly is in the upper position, and to de-energize the radiant heater and energize the convective heater when the assembly is in the lower position.

19. Apparatus according to claim 18, further comprising a humidifier cooperating with the convective heater to add moisture to the air within the enclosure.

20. Apparatus according to claim 19, wherein said controller has an output coupled to the humidifier.

21. Apparatus according to claim 18, further comprising a fan, and wherein said controller has an output coupled to the fan.

22. Apparatus according to claim 21, wherein the fan is energized by the controller when the assembly is in the lower position.

23. Apparatus according to claim 18, further comprising an air temperature sensor having an output and being configured to produce a signal indicative of air temperature in the apparatus.

24. Apparatus according to claim 23, wherein the output of the air temperature sensor is coupled to the controller.

25. Apparatus according to claim 18, further comprising a patient temperature sensor having an output and being configured to produce a signal indicative of the temperature of the patient.

26. Apparatus according to claim 25, wherein the output of the patient temperature sensor is coupled to the controller.

27. A patient warming apparatus, comprising:
   a) a patient support;
   b) a canopy associated with the patient support to provide an enclosure for the patient;
   c) a radiant heater;
   d) a convective heater disposed to warm the enclosure;
   e) the canopy being movable upwardly away from the support to expose the patient thereon;
   f) the radiant heater being disposed to heat the patient on the support when the canopy is raised to expose the patient; and
   g) a controller having a first output coupled to the convective heater and a second output coupled to the radiant heater, the controller operating to energize the radiant heater when the canopy is raised to expose the patient, and to de-energize the radiant heater and energize the convective heater when the canopy and support provide an enclosure.

* * * * *